United States Patent
Il et al.

(10) Patent No.: US 10,842,876 B2
(45) Date of Patent: Nov. 24, 2020

(54) STATIN-CONTAINING NANOPARTICLE PREPARATION FOR ENHANCING FUNCTION OF STEM CELLS FOR TREATING INFLAMMATORY DISEASE, AND FUNCTIONALLY ENHANCED STEM CELLS CONTAINING SAME FOR TREATING INFLAMMATORY DISEASE

(71) Applicant: EDUCATIONAL FOUNDATION OF OSAKA MEDICAL AND PHARMACEUTICAL UNIVERSITY, Takatsuki (JP)

(72) Inventors: Masaaki Il, Takatsuki (JP); Yasuhiko Tabata, Kyoto (JP)

(73) Assignee: EDUCATIONAL FOUNDATION OF OSAKA MEDICAL AND PHARMACEUTICAL UNIVERSITY, Takatsuki (JP)

( * ) Notice: Subject to any disclaimer, the term of this patent is extended or adjusted under 35 U.S.C. 154(b) by 0 days.

(21) Appl. No.: 16/098,838

(22) PCT Filed: Apr. 27, 2017

(86) PCT No.: PCT/JP2017/016858
§ 371 (c)(1),
(2) Date: Nov. 2, 2018

(87) PCT Pub. No.: WO2017/191808
PCT Pub. Date: Nov. 9, 2017

(65) Prior Publication Data
US 2019/0134201 A1    May 9, 2019

(30) Foreign Application Priority Data

May 6, 2016 (JP) .................................. 2016-093398
Aug. 26, 2016 (JP) .................................. 2016-166299

(51) Int. Cl.
*A61K 9/00* (2006.01)
*A61K 47/34* (2017.01)
(Continued)

(52) U.S. Cl.
CPC ............ *A61K 47/34* (2013.01); *A61K 9/0014* (2013.01); *A61K 9/51* (2013.01); *A61K 31/366* (2013.01);
(Continued)

(58) Field of Classification Search
CPC ....................................................... A61K 47/34
See application file for complete search history.

(56) References Cited

U.S. PATENT DOCUMENTS

2010/0086602 A1    4/2010 Egashira
2010/0086615 A1    4/2010 Egashira
(Continued)

FOREIGN PATENT DOCUMENTS

EP    3 231 443 A1    10/2017
JP    2012-021002 A    2/2012
(Continued)

OTHER PUBLICATIONS

Machine Translation of JP 201221002A to Kyushu University, Mar. 27, 2019.*

(Continued)

*Primary Examiner* — Paul W Dickinson
(74) *Attorney, Agent, or Firm* — Knobbe, Martens, Olson & Bear, LLP

(57) ABSTRACT

A statin-encapsulated nanoparticle contains a bioabsorbable polymer and statin encapsulated in the nanoparticle. Suitable bioabsorbable polymers include a polylactic acid (PLA) polymer or a polylactic acid-glycolic acid (PLGA) copolymer. The statin-encapsulated nanoparticle can be used to (Continued)

enhance the function of a stem cell. The stem cell can be a stem cell for treating an inflammatory disease.

9 Claims, 12 Drawing Sheets

(51) Int. Cl.
  *A61K 9/51* (2006.01)
  *A61K 35/28* (2015.01)
  *A61K 31/366* (2006.01)
  *A61K 45/00* (2006.01)
  *C08L 67/04* (2006.01)
  *B82Y 5/00* (2011.01)

(52) U.S. Cl.
  CPC .............. *A61K 35/28* (2013.01); *A61K 45/00* (2013.01); *C08L 67/04* (2013.01); *B82Y 5/00* (2013.01); *C08L 2203/02* (2013.01)

(56) References Cited

U.S. PATENT DOCUMENTS

| | | |
|---|---|---|
| 2014/0154274 A1 | 6/2014 | Lombardo |
| 2016/0000831 A1 | 1/2016 | Chang |

FOREIGN PATENT DOCUMENTS

| | | |
|---|---|---|
| JP | 2012-157263 A | 8/2012 |
| JP | 2014-502628 A | 2/2014 |
| KR | 10-2015-0144679 | 12/2015 |
| WO | WO 2016/076227 A1 | 5/2016 |

OTHER PUBLICATIONS

Machine Translation of JP 2012157263A to Seems, Inc, Mar. 27, 2019.*
Machine Translation of JP 2014502628A to Tigenix, S.A.U., Mar. 27, 2019.*
Yokoyama et al, Unique Therapeutic Effect of Statin Nanoparticle-Loaded Adipose-Derived Stem Cells on Myocardial Infarction, Circulation, 2014, 130:A12138.*
Abe, Y., et al., Possibility to Tissue Remodeling and Anti-Fibrotic Properties of Simvastatin on TNBS-Induced Colitis Model, Ulcer Research, vol. 37, No. 2, pp. 169-173, 2010.
Cai, A., et al., Atorvastatin Treatment of Rats With Ischemia-Reperfusion Injury Improves Adipose-Derived Mesenchymal Stem Cell Migration and Survival Via The SDF-1 α/CXCR-4 Axis, PLOS One, vol. 8, No. 12, e79100, 2013.
Gonzalez, M.A., et al., AdiposeDerived Mesenchymal Stern Cells Alleviate Experimental Colitis by Inhibiting Inflammatory and Autoimmune Responses, Gastroenterology, vol. 136, pp. 978-989, 2009.
Grip, O., et al., Use of atorvastatin as an anti-inflammatory treatment in Crohn's disease, British Journal of Pharmacology, vol. 155, pp. 1085-1092, 2008.
International Search Report, dated Jul. 4, 2017, in International Application No. PCT/JP2017/016858.
Wang, C.-Z., et al., Synthesis and Characterization of Cationic Polymeric Nanoparticles as Simvastatin Carriers for Enhancing the Osteogenesis of Bone Marrow Mesenchymal Stem Cells, Journal of Colloid and Interface Science, vol. 432, pp. 190-199, 2014.
Yokoyama, R., et al., Unique Therapeutic Effect of Statin Nanoparticle-Loaded Adipose-Derived Stem Cells on Myocardial Infarction, Circulation, vol. 130, Suppl. 2, Abstract 12139, 2014.
Kakimoto K., et al., A Novel Hybrid Treatment with Simvastin-Conjugated Biodegradeable Nanoparticle and Adipose-Derived Stem Cells Enhances the Therapeutic Activity in a Mouse Model of Colitis, Gastroenterology, AGA Abstracts, Apr. 22, 2017. (Abstract Only).
Extended European Search Report, dated Dec. 11, 2019, for European Application No. 17792741.5.
Atherosclerosis and inflammation, Vascular Medicine, vol. 4, No. 5, pp. 461-463, 2003.
Notification of Reasons for Refusal, dated Apr. 14, 2020, in KR Patent Application No. 10-2018-7034459.
Notification of Reasons for Refusal, dated Apr. 23, 2020, in JP Patent Application No. 2018-515716.
Therapeutics, vol. 40, No. 3, pp. 273-277, 2006.
Examination Report, dated Feb. 19, 2020, in Indian Patent Application No. 201817044039.
Office Action dated Aug. 7, 2020 in Chinese Application No. 201780027140.X.

\* cited by examiner

[FIG.1]
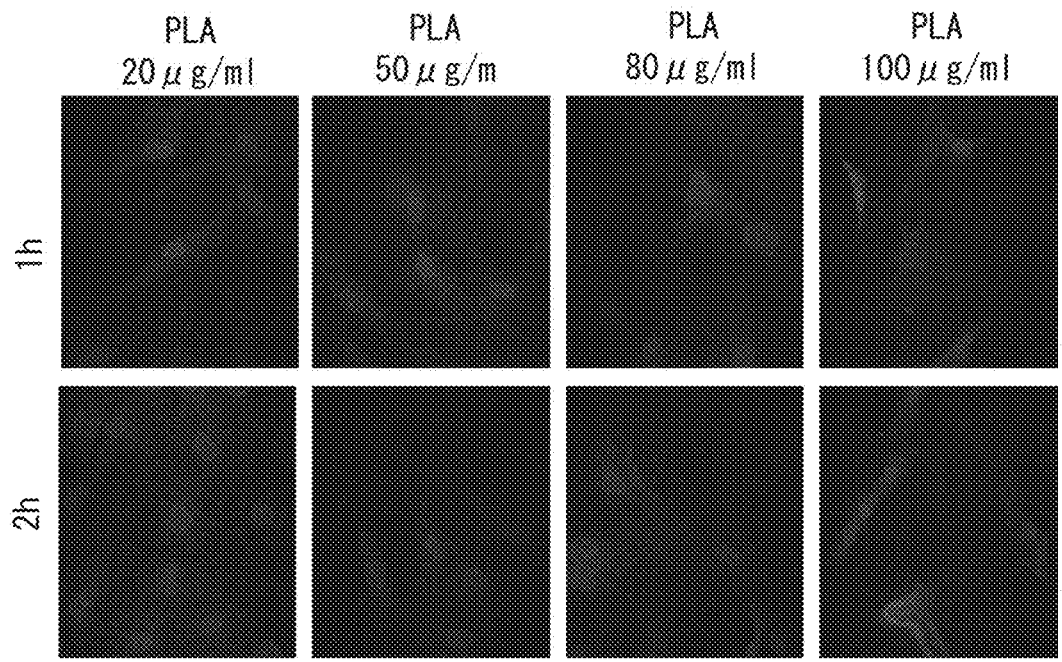
[FIG.2]
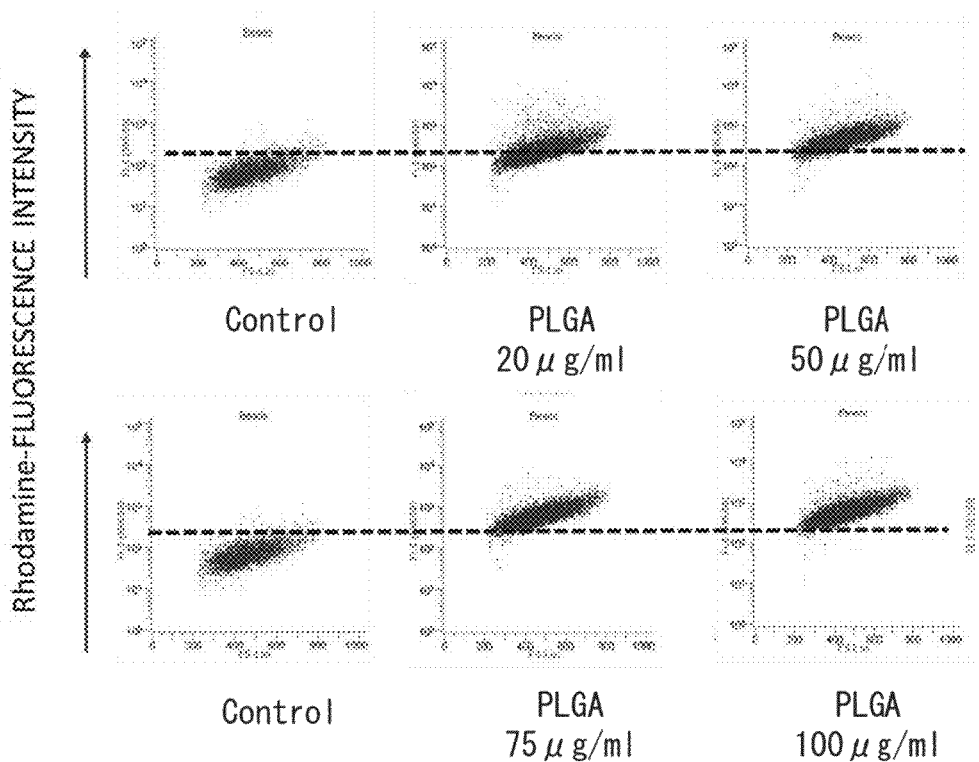

[FIG.3]
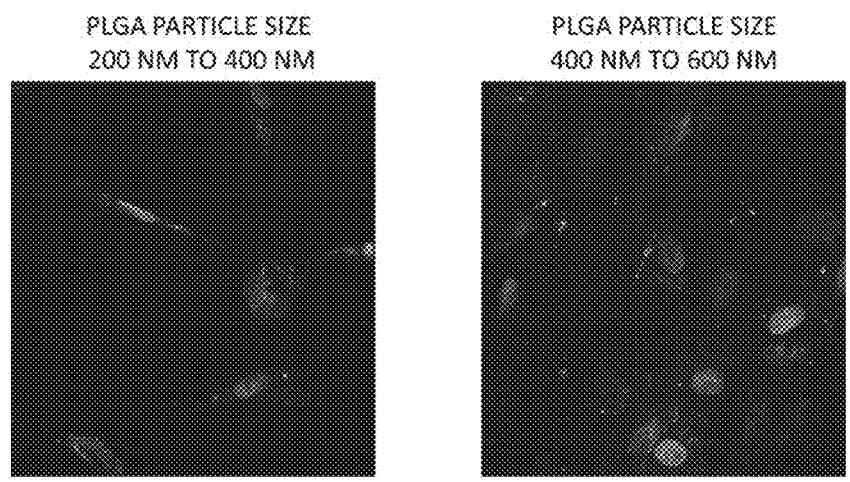
[FIG.4]
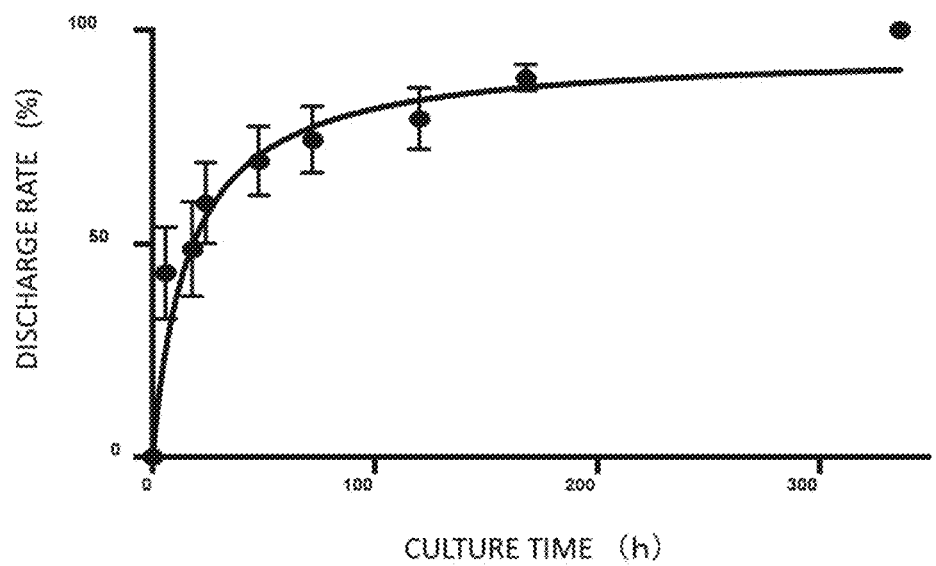

[FIG.5]
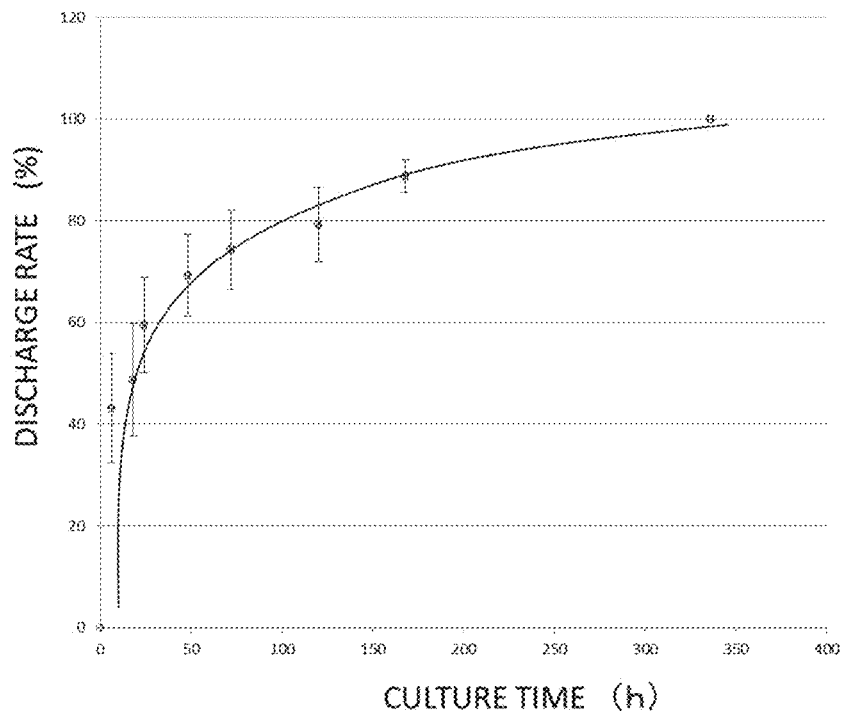
[FIG.6]
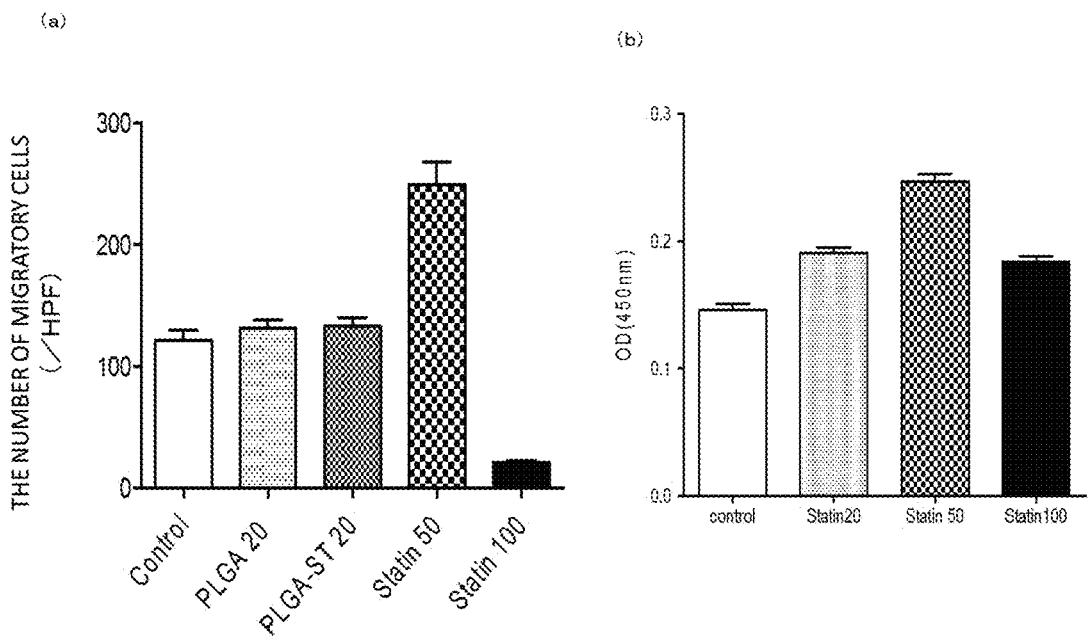

[FIG.7]
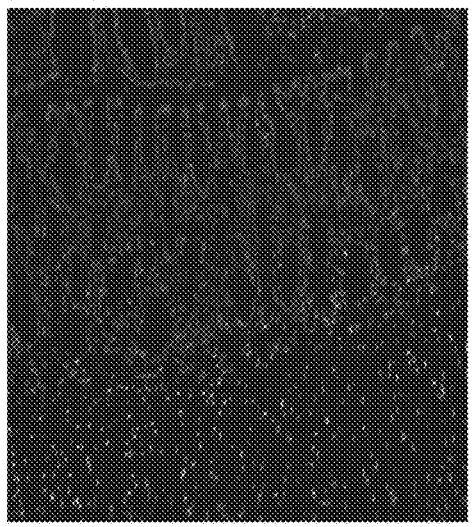 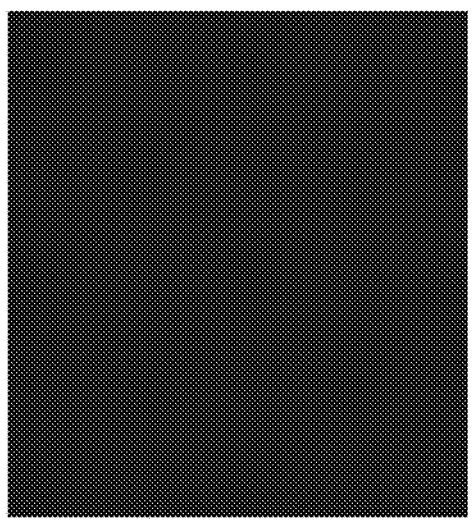
DAPI STAIN　　　　　　　　　　　　　　Rhodamine
[FIG.8]
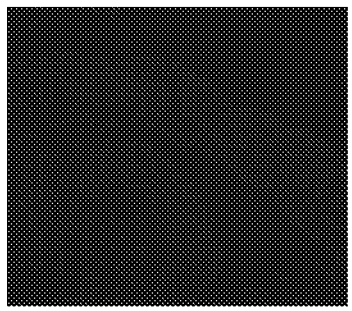 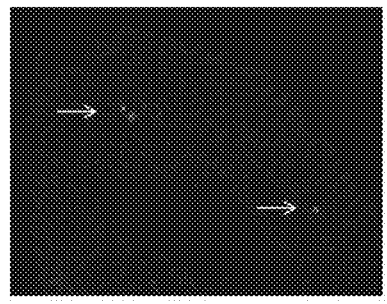 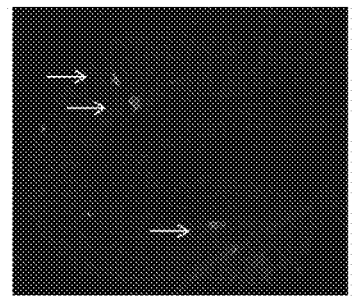
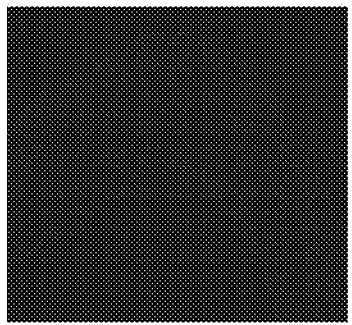 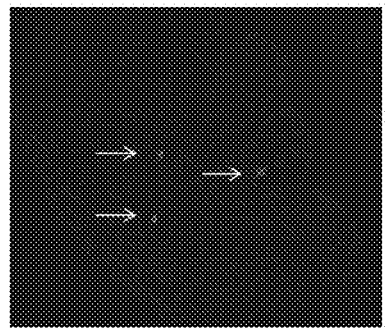 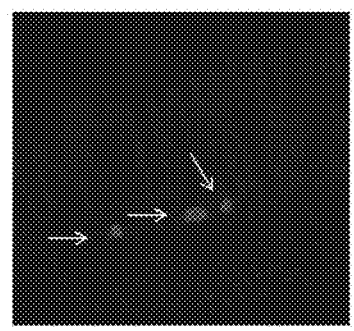
2 × 10⁴ cells　　　　　　　1 × 10⁵ cells　　　　　　　3 × 10⁵ cells

[FIG.9]
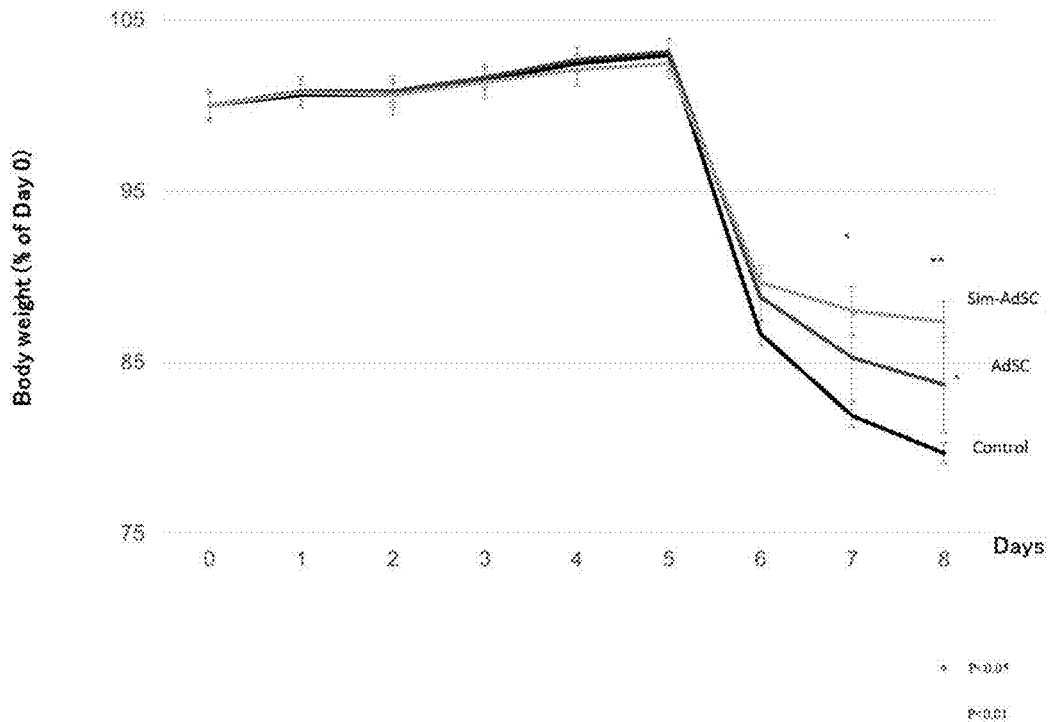
[FIG.10]
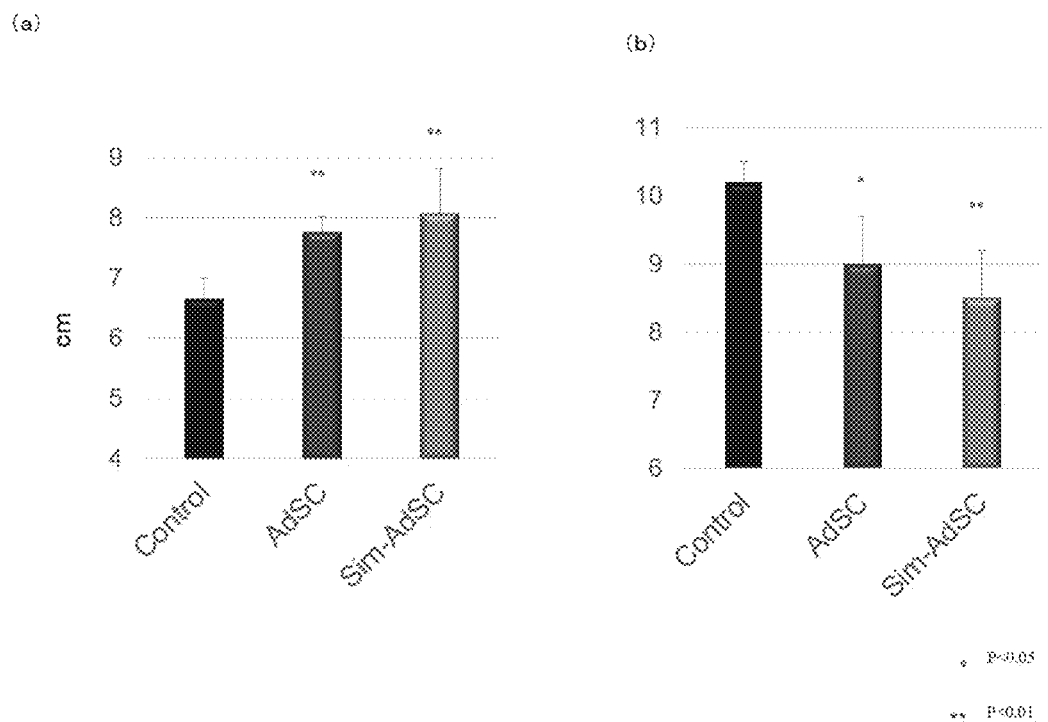

[FIG.11]

TABLE Disease Activity Index Score (DAI score)
(Sutherland L.R. Gastroenterology 92 : 1894, 1987)

| | | |
|---|---|---|
| THE NUMBER OF TIMES OF DEFECATION | 0 | NORMAL |
| | 1 | ONE TO TWO TIMES MORE THAN NORMAL |
| | 2 | THREE OR FOUR TIMES MORE THAN NORMAL |
| | 3 | FIVE OR MORE TIMES MORE THAN NORMAL |
| HEMATOCHEZIA | 0 | NONE |
| | 1 | LITTLE |
| | 2 | OBVIOUS |
| | 3 | ALMOST ALL HEMATOCHEZIA |
| ENDOSCOPE VIEWS (Baron CLASSIFICATION) | 0 | NORMAL |
| | 1 | MINOR |
| | 2 | MODERATE |
| | 3 | SERIOUS |
| TOTAL EVALUATION BY MEDICAL DOCTOR | 0 | NORMAL |
| | 1 | MINOR |
| | 2 | MODERATE |
| | 3 | SERIOUS |

[FIG.12]
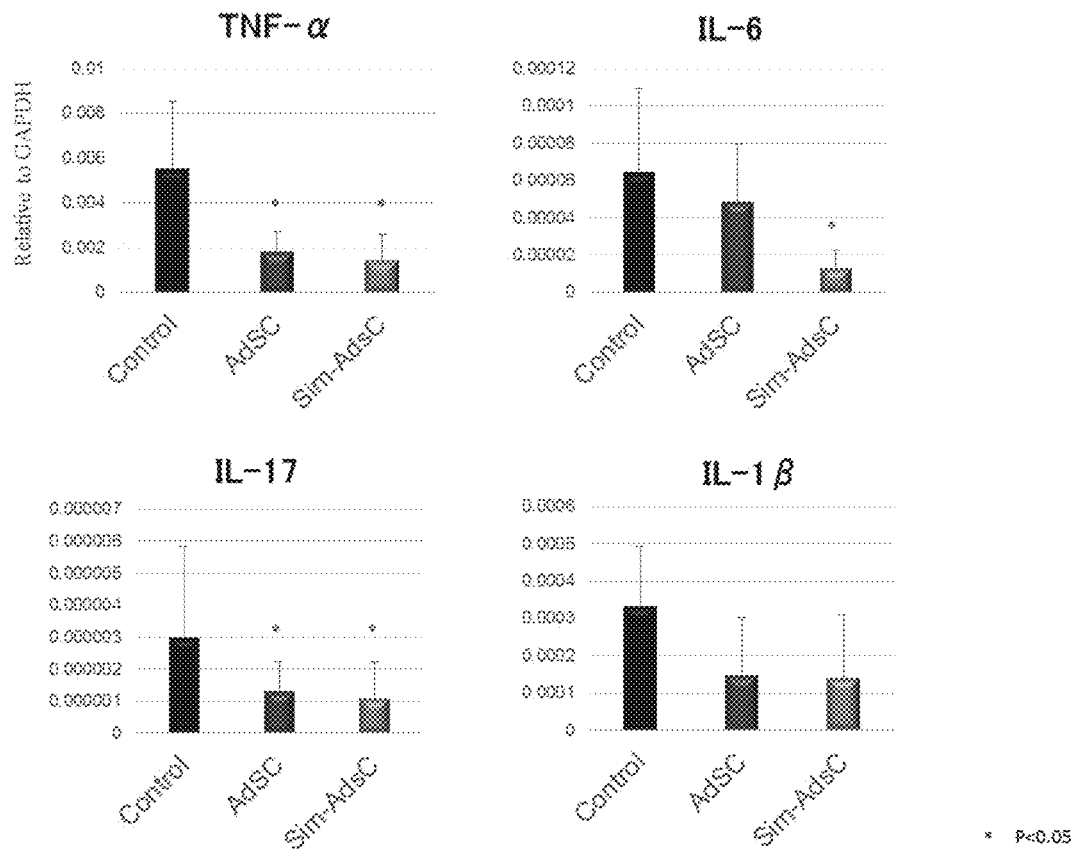
[FIG.13]
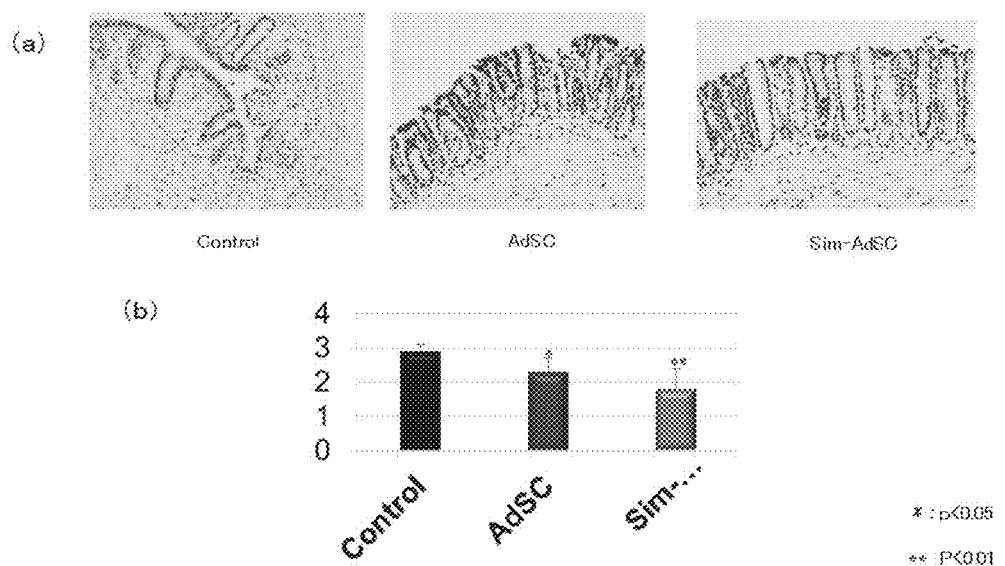

[FIG.14]
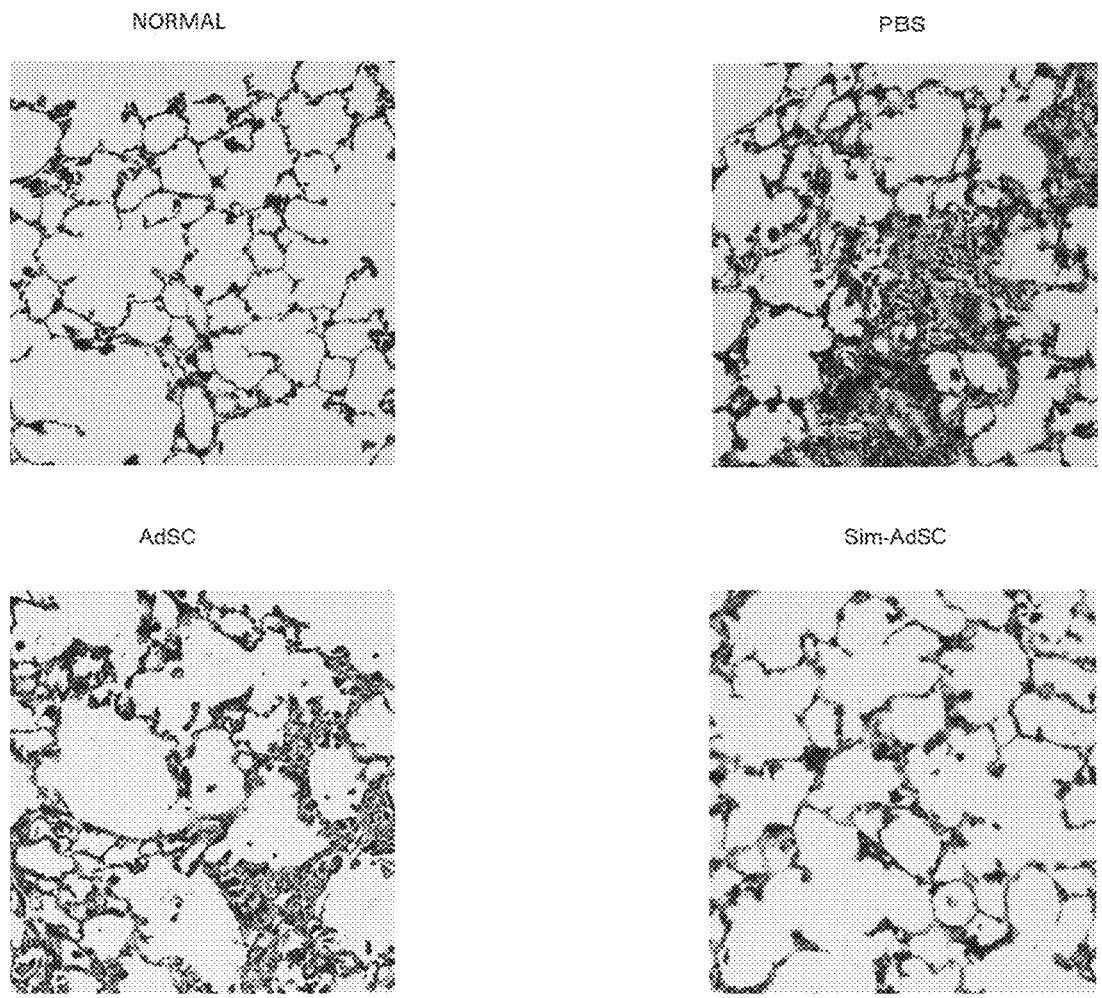

[FIG.15]
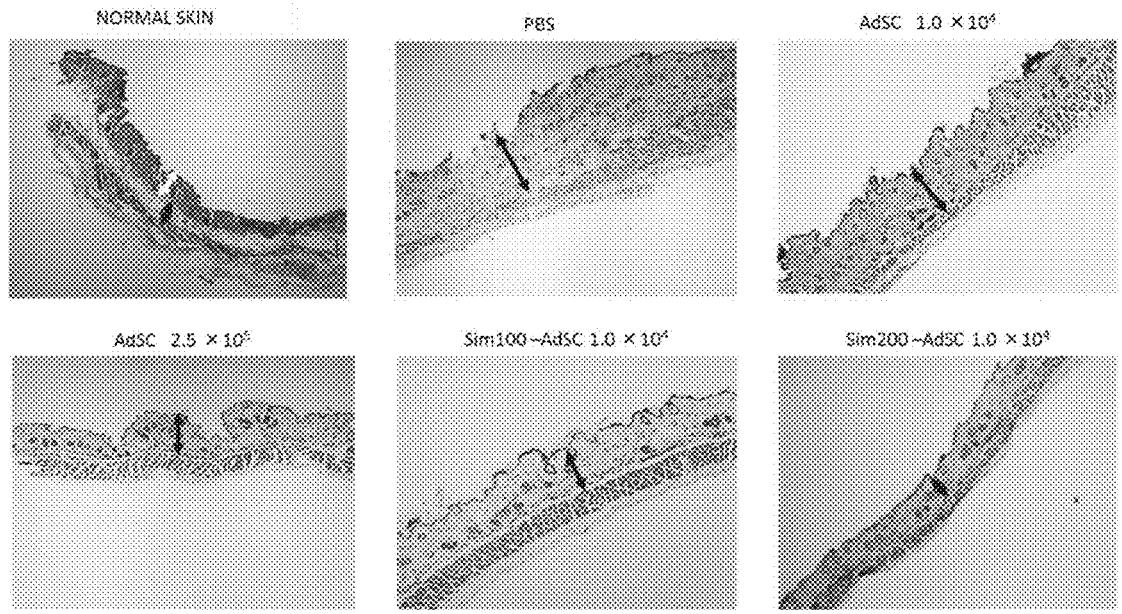
[FIG.16]
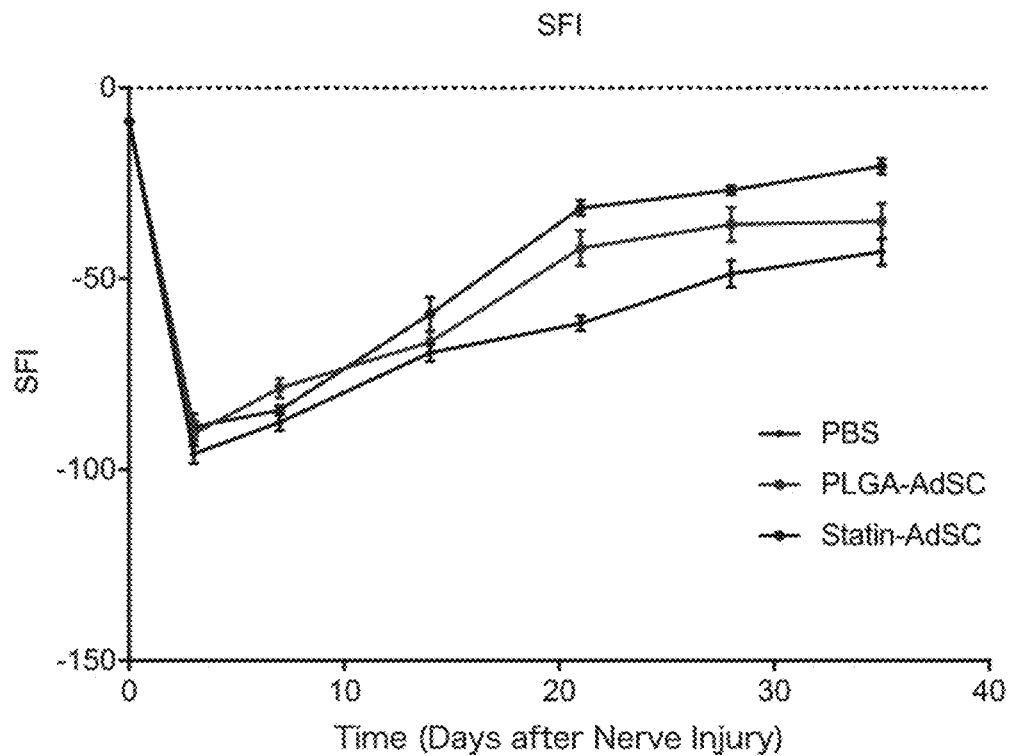

[FIG.17]
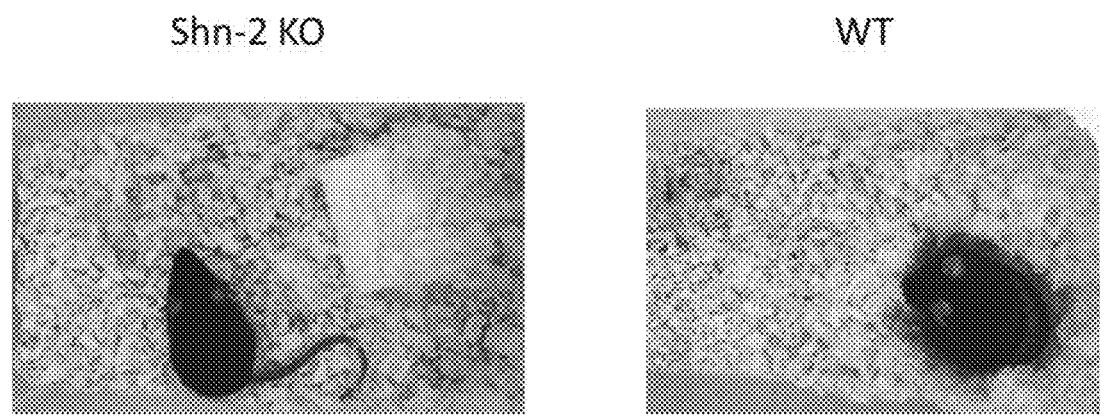
[FIG.18]
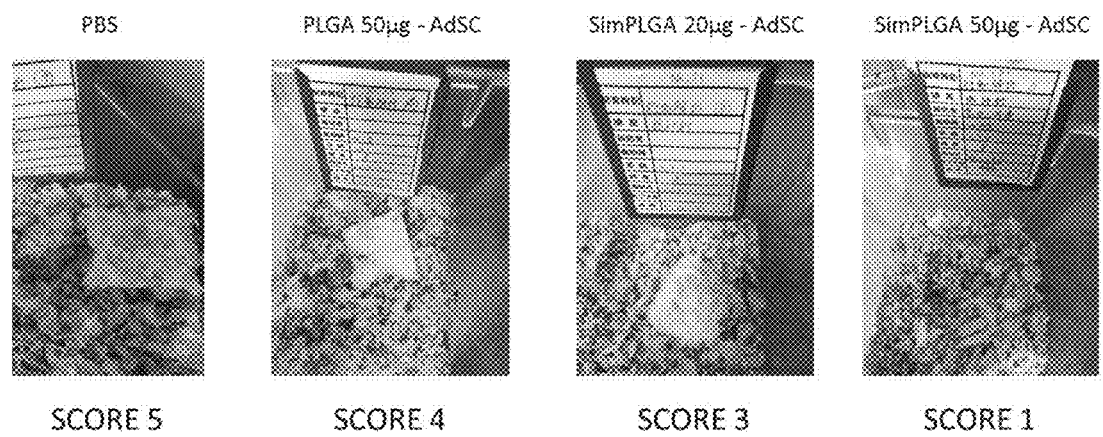

[FIG.19]
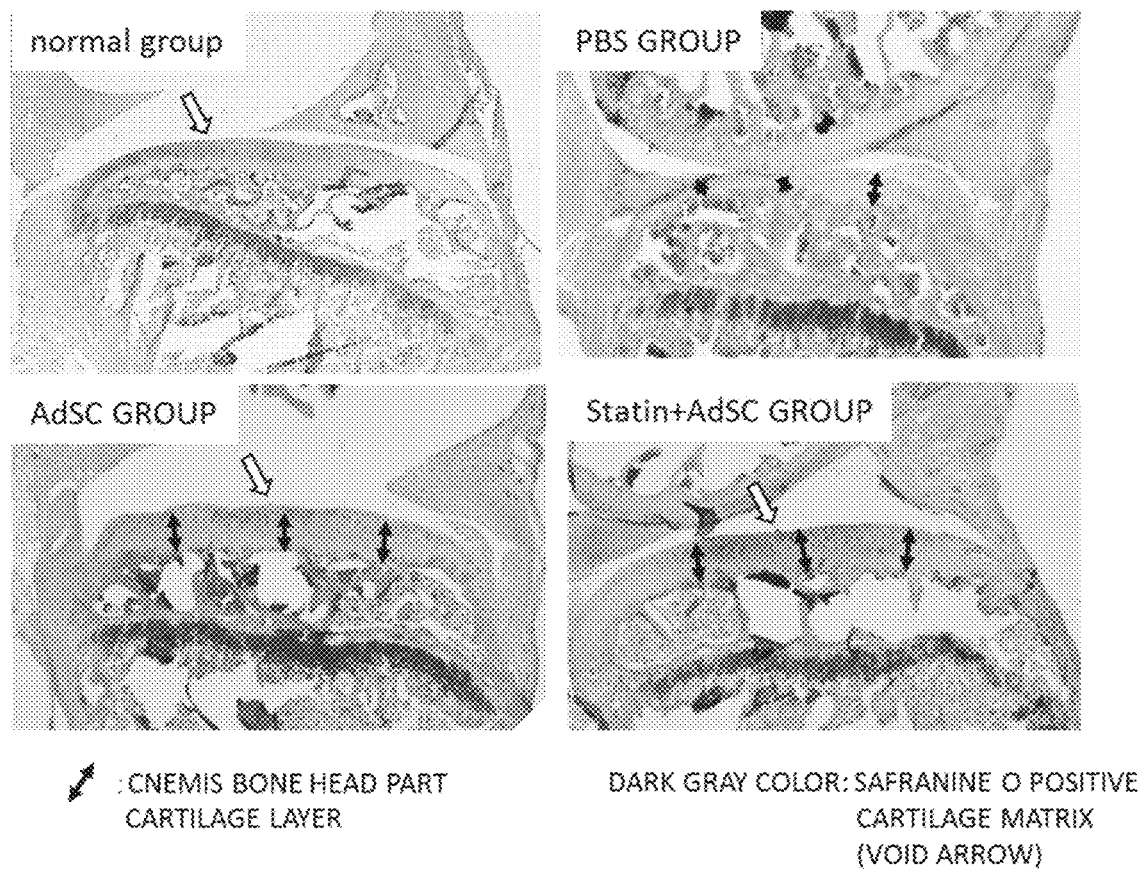
↗ : CNEMIS BONE HEAD PART CARTILAGE LAYER
DARK GRAY COLOR: SAFRANINE O POSITIVE CARTILAGE MATRIX (VOID ARROW)
[FIG.20]
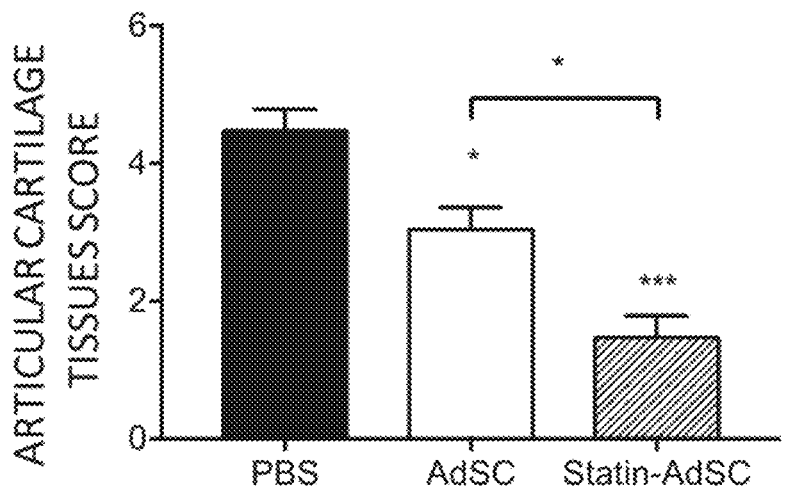
* and ***, P<0.05 and 0.001 vs. PBS (n=3)

[FIG.21]
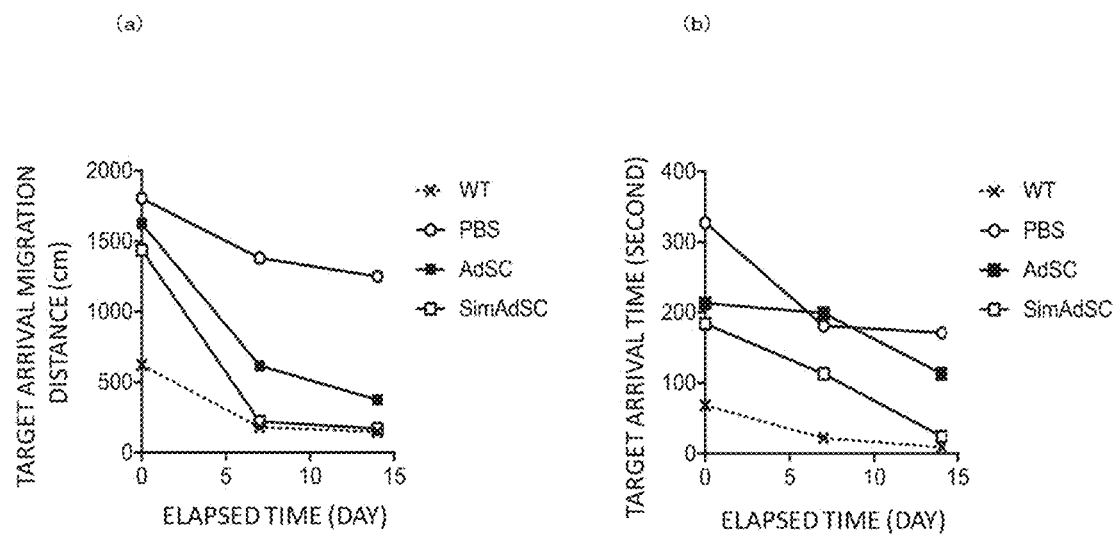

STATIN-CONTAINING NANOPARTICLE PREPARATION FOR ENHANCING FUNCTION OF STEM CELLS FOR TREATING INFLAMMATORY DISEASE, AND FUNCTIONALLY ENHANCED STEM CELLS CONTAINING SAME FOR TREATING INFLAMMATORY DISEASE

CROSS REFERENCE TO RELATED APPLICATIONS

This application is the U.S. National Stage Application under 35 U.S.C. § 371 of International Application No. PCT/JP2017/016858, filed Apr. 27, 2017, designating the U.S. and published as WO 2017/191808 A1 on Nov. 9, 2017, which claims the benefit of Japanese Patent Application No. JP 2016-166299, filed Aug. 26, 2016, and Japanese Patent Application No. JP 2016-093398, filed May 6, 2016. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to statin-included nanoparticles and specifically, to a statin-included nanoparticle (particle used in a preparation, a preparation containing the statin-included nanoparticle, or the like) for enhancing the function of a cell for treating inflammatory diseases. Moreover, the present invention relates to a stem cell containing a statin-included nanoparticle for treating inflammatory diseases.

BACKGROUND ART

Statin is known as a compound which inhibits HMG-CoA reductase which is a rate-limiting enzyme of cholesterol biosynthesis in the liver. Statin can reduce the cholesterol level in blood and is thus used in therapeutic drugs for hypercholesterolemia. Moreover, clinical tests have revealed that statin is also effective to ischemic heart diseases such as angina pectoris and myocardial infarction and diseases such as arteriosclerosis due to the anti-inflammatory activity of the statin in addition to hypercholesterolemia.

Various studies have been conducted to improve the therapeutic effect of statin on the above-described diseases and to reduce side effects caused by the statin. For example, Patent Literature 1 discloses that in a case of administration of statin for acceleration of neovascularization, the statin is included in nanoparticles, and the statin-included nanoparticles are topically administered to patients, thereby enabling the acceleration of the neovascularization with a fewer amount of statin than before.

As described above, statin exhibits various activities and in particular, has anti-inflammatory activity, and therefore, application of the statin to inflammatory diseases has been actively studied. For example, Non-Patent Literature 1 discloses that simvastatin which is a type of statin exhibits anti-inflammatory activity in a mouse inflammatory bowel disease model. Moreover, Non-Patent Literature 2 describes an anti-inflammatory effect of atorvastatin on patients suffering from Crohn's disease.

Moreover, in recent years, studies of treating various diseases with pluripotent stem cells have been conducted. Examples of stem cells generally include embryonic stem cells (ES cells) and mesenchymal somatic stem cells such as bone marrow-derived stem cells and adipose derived stem cells, and additionally, induced pluripotent stem cells (iPS cells) and the like, and such cells are adopted in various studies. Among them, the study of adipose derived stem cells which are easily handleable is rapidly developing, and clinical tests of regenerative medicine for various diseases are widely performed. It is also reported that adipose derived stem cells exhibit an enteritis depression effect in a drug-induced enteritis mouse model in addition to use in the regenerative medicine (for example, see Non-Patent Literature 3).

CITATION LIST

Patent Literature

[Patent Literature 1] Japanese Laid-Open Patent Publication No. 2012-21002

Non-Patent Literature

[Non-Patent Literature 1] Yosuke, Abe et al., Ucer, 37(2010), 169-173.
[Non-Patent Literature 2] Grip, O et al, Br J Pharmacol. 155(2008), 1085-1092.
[Non-Patent Literature 3] Gonzalez, M A et al. Gastroenterology 136(2009), 978-989.

SUMMARY

In order to enable the effect of statin to be more efficiently exhibited in treatment of inflammatory diseases by using the statin as disclosed in, for example, Non-Patent Literatures 1 and 2, the statin may be included in nanoparticles to obtain statin-included nanoparticles, which may be administered to patients as disclosed in, for example, Patent Literature 1. However, in Patent Literature 1, the statin-included nanoparticles are topically administered to patients. Thus, the effectiveness is confirmed with a smaller amount of the statin than before, but the statin nanoparticles administered are, for example, phagocytized by macrophages, and are likely to be non-uniformly distributed in lesions, and therefore, there may be cases where a stable therapeutic effect is hardly obtained.

Meanwhile, also when inflammatory diseases are treated with only stem cells as disclosed in Non-Patent Literature 3, topical administration of the stem cells to a diseased part is required, and an enormous volume of cells are required. Therefore, not only cost and time are required, but also the frequency of occurrence of side effect of cell administration may increase. Moreover, when autologous cell transplant is assumed, in a case where the number of fat tissues is small and the number of separable stem cells is thus small or in a case where the stem cell function is degraded due to factors of turnover diseases such as an advanced age and/or diabetes mellitus, various types of functions of the stem cells have to be improved in order to obtain excellent therapeutic effects from a small number of stem cells.

In view of the foregoing, the present invention was realized. It is an object of the present invention to enable the function of a stem cell used as a cell preparation or the like to be improved while the therapeutic effect of the stem cell on inflammatory diseases is improved and side effects of the stem cell are reduced.

To achieve the object, the present inventors conducted intensive studies. As a result, the present inventors found that a statin-included nanoparticle obtained by including statin in a nanoparticle is contained in a stem cell to enhance the function of the stem cell, which enables efficient delivery and the like of the statin to a diseased part desired and shows a high effectiveness in treatment of inflammatory diseases, and inventors completed the present invention. That is, a statin-included nanoparticle according to the present invention is a statin-included nanoparticle including: a nanoparticle containing a bioabsorbable polymer; and statin included in the nanoparticle, the statin-included nanoparticle being a particle for enhancing a function of a stem cell, the stem cell being a stem cell for treating an inflammatory disease.

Treating a stem cell with the statin-included nanoparticle according to the present invention (specifically, the nanoparticle is incorporated into the stem cell) enables the function of the treated stem cell to be enhanced, and administering the treated stem cell into a living body produces various types of effectiveness. Specifically, when a stem cell is treated with the statin-included nanoparticle according to the present invention, the treated stem cell takes up the statin-included nanoparticle through phagocytosis, which enhances the immunosuppression capacity, in in addition to the migratory capacity and the proliferative capacity, of the stem cell which has taken up the statin-included nanoparticle. Thus, when the stem cell treated with the statin-included nanoparticle according to the present invention is administered into the body of a patient suffering from, for example, an inflammatory disease, enhanced immunosuppression activity of the stem cell and anti-inflammatory activity of statin control-released from the stem cell exhibit an excellent therapeutic effect on inflammatory diseases.

In the statin-included nanoparticle according to the present invention, poly lactic acid (PLA) or poly(lactic co-glycolic acid (PLGA) may be used as the bioabsorbable polymer.

Hydrolysis of the PLA and the PLGA in a body enables included statin to be released. Moreover, the hydrolysis of the PLA decomposes the PLA into lactic acid, and the hydrolysis of the PLGA decomposes the PLGA into lactic acid and glycol, which are eventually decomposed into water and carbon dioxide gas respectively, and are harmless to animal such as humans. Therefore, the PLA or the PLGA is very preferably used as a nanoparticle material.

The statin-included nanoparticle according to the present invention is preferably configured to enhance a mesenchymal stem cell, in particular, an adipose derived stem cell as the above-described stem cell.

To obtain adipose derived stem cells, fat tissues are collected, the collected tissues are subjected to collagenase treatment, only mononuclear leukocyte cells are then collected by a centrifugal specific gravity method, the collected mononuclear leukocyte cells are incubated for about 4 days in an incubation plate, and bonded cells can be selected and separated as the adipose derived stem cells. Moreover, a large quantity of adipose derived stem cells can be easily extracted, separated, and incubated from fat tissues by using Celution system (manufactured by Cytori Therapeutics, Inc.) or the like. The adipose derived stem cells belong to mesenchymal stem cells, also have multipotency, can be easily collected at a large quantity as described above, and are thus advantageously used for regenerative medicine in various types of diseases. Moreover, the adipose derived stem cells produce and emit anti-inflammatory cytokines and downregulate the activity of inflammatory cells, and are thus advantageous for treating inflammatory diseases.

Moreover, a functionally enhanced stem cell according to the present invention has features of containing statin-included nanoparticles obtained by including the statin in biocompatibility nanoparticles and adopted for treating an inflammatory disease.

The functionally enhanced stem cell according to the present invention contains the statin-included nanoparticles. Therefore, as described above, the statin-included nanoparticles enhance cell functions such as immunosuppression capacity, and the functionally enhanced stem cell can exhibit excellent effect for treating an inflammatory disease. Moreover, the cell with enhanced function according to the present invention can gradually release statin and is advantageous for treating inflammatory diseases due to the anti-inflammatory activity of the released statin.

For the reasons described above, the functionally enhanced stem cell according to the present invention is preferably the adipose derived stem cell.

Moreover, the functionally enhanced stem cell according to the present invention may be in preparation form as a cell preparation obtained by mixing the stem cell with a pharmaceutically acceptable solvent and a vehicle. The stem cell according to the present invention is preferably administered to a living body without requiring an operation such as abdominal section, and is preferably in preparation form as a cell preparation for intravenous or intra-arterial administration. In this way, the stem cell according to the present invention can be easily administered to patients. In a functionally enhanced stem cell preparation according to the present invention, the function of the stem cell is enhanced, and therefore, even with the intravenous administration or the intra-arterial administration, it is possible to obtain high effect with a small administration amount. Moreover, intra-arterial administration of the functionally enhanced stem cell preparation according to the present invention enables stem cells to be accumulated at inflammation sites such as intestine and the like. The intravenous administration hardly enables the stem cells to arrive at the intestine. Thus, adopting the intra-arterial administration may enable a small amount of cells to be distributed in lesion uniformly to obtain stable and high effect. Moreover, the functionally enhanced stem cell preparation according to the present invention may be topically administered as long as a certain desired effect can be obtained.

A statin-included nanoparticle and a functionally enhanced stem cell containing the statin-included nanoparticle according to the present invention enable the function of a stem cell to be enhanced, and administering the stem cell to a living body produces excellent effect for treating inflammatory diseases.

BRIEF DESCRIPTION OF DRAWINGS

FIG. 1 shows photographs of a result of observation of human adipose derived stem cells in incubation media observed with a confocal laser fluorescence microscope one hour or two hours after addition of rhodamine red fluorescent stain-included PLA nanoparticles to the incubation media so as to achieve a final concentration of 20 µg/mL, 50 µg/mL, 80 µg/mL, or 100 µg/mL.

FIG. 2 shows photographs of a result obtained by measuring the uptake quantity of rhodamine red fluorescent stain-included PLGA nanoparticles in the stem cells with FACS 30 minutes after addition of the rhodamine red fluorescent stain-included PLGA nanoparticles to the incubation media of mouse adipose derived stem cells so as to achieve a final concentration of 20 μg/mL, 50 μg/mL, 75 μg/mL, or 100 μg/mL.

FIG. 3 shows photographs of a result of observation of human adipose derived stem cells in incubation media with a confocal laser fluorescence microscope one hour after addition of rhodamine red fluorescent stain-included PLGA nanoparticles having a grain size of 200 nm to 400 nm or 400 nm to 600 nm.

FIG. 4 is a graph illustrating a result obtained by measuring the amount of simvastatin released from adipose derived stem cells into a medium, the amount being measured after treatment of human adipose derived stem cells with simvastatin-included PLA nanoparticles at a concentration of 100 μg/mL for one hour.

FIG. 5 is a graph illustrating a result obtained by measuring the amount of simvastatin released from adipose derived stem cells into a medium, the amount being measured after treatment of mouse adipose derived stem cells with simvastatin-included PLA nanoparticles at a concentration of 50 μg/mL for 30 minutes.

FIG. 6(a) is a graph illustrating measurement results of the migratory property of human adipose derived stem cells treated with PLA nanoparticles or statin-included PLA nanoparticles, and FIG. 6(b) is a graph illustrating measurement results of the proliferation characteristic of human adipose derived stem cells treated with statin-included PLA nanoparticles.

FIG. 7 shows photographs of a result of observation of the large intestine of a mouse to which mouse adipose derived stem cells including rhodamine red fluorescent stain-included PLGA nanoparticles are intravenously administered with a confocal laser fluorescence microscope.

FIG. 8 shows photographs of a result of observation of the large intestine of a mouse to which mouse adipose derived stem cells including rhodamine red fluorescent stain-included PLGA nanoparticles are intra-arterially administered with a confocal laser fluorescence microscope.

FIG. 9 is a graph illustrating a variation with time of the body weights of DSS enteritis model mice each administered with phosphoric acid buffer (PBS), statin-non-included nanoparticle containing adipose derived stem cells, or statin-included nanoparticle containing adipose derived stem cells.

FIG. 10(a) is a graph illustrating the lengths of large intestines of the DSS enteritis model mice each administered with PBS, statin-non-included nanoparticle containing adipose derived stem cells, or statin-included nanoparticle containing adipose derived stem cells, and FIG. 10(b) is a graph illustrating DAI scores of the DSS enteritis model mice each administered with PBS, statin-non-included nanoparticle containing adipose derived stem cells, or statin-included nanoparticle containing adipose derived stem cells.

FIG. 11 is a table illustrating the DAI score.

FIG. 12 shows graphs illustrating gene expression amount of TNFα, IL-17, IL-6, and IL-1β in the DSS enteritis model mice each administered with PBS, statin-non-included nanoparticle containing adipose derived stem cells, or statin-included nanoparticle containing adipose derived stem cells.

FIG. 13(a) shows photographs illustrating a result of a histological analysis of the large intestine of the DSS enteritis model mice each administered with PBS, statin-non-included nanoparticle containing adipose derived stem cells, or statin-included nanoparticle containing adipose derived stem cells, and FIG. 13(b) is a graph showing scores on the histological analysis.

FIG. 14 shows photographs illustrating a result of a histological analysis of lungs of normal mice and interstitial pneumonia model mice each administered with PBS, statin-non-included nanoparticle containing adipose derived stem cells, or statin-included nanoparticle containing adipose derived stem cells.

FIG. 15 shows photographs illustrating a result of a histological analysis of skin of normal mice and scleroderma model mice each administered with PBS, statin-non-included nanoparticle containing adipose derived stem cells, or statin-included nanoparticle containing adipose derived stem cells.

FIG. 16 is a graph illustrating a result of measurement of sciatic nerve function index (SFI) of nerve injury model mice each administered with PBS, statin-non-included nanoparticle containing adipose derived stem cells, or statin-included nanoparticle containing adipose derived stem cells.

FIG. 17 shows photographs illustrating a result of a nesting action analysis of normal mice and Shn-2KO mice.

FIG. 18 shows photographs illustrating a result of a nesting action analysis of a Shn-2KO mouse administered with PBS, statin-non-included nanoparticle containing adipose derived stem cells, or statin-included nanoparticle containing adipose derived stem cells.

FIG. 19 is photographs illustrating a result of a histological analysis of articular cartilage tissues of normal mice and osteoarthritis model mice each administered with PBS, human adipose derived stem cells, or statin-included nanoparticle containing human adipose derived stem cells.

FIG. 20 is a graph illustrating a result of scoring the joint injury degree of osteoarthrosis model mice each administered with PBS, human adipose derived stem cells, or statin-included nanoparticle containing human adipose derived stem cells.

FIGS. 21(a) and 21(b) show a result of memory analysis of normal mice and dementia model mice each administered with PBS, mouse adipose derived stem cells, or statin-included nanoparticle containing mouse adipose derived stem cells, wherein FIG. 21(a) is a graph illustrating migration distances of mice which find a target hole and enter an escape cage in a Barnes maze test, and FIG. 21(b) is a graph illustrating times until the mice enter the escape cage.

DETAILED DESCRIPTION

Embodiments of the present invention will be described below with reference to the drawings. The following description of preferable embodiments is substantially a mere example and does not intend to limit the present invention, application methods, or applications thereof.

A statin-included nanoparticle according to the present invention is a statin-included nanoparticle which is obtained by including statin in a nanoparticle (which includes a nanoparticle and statin included in the nanoparticle), the nanoparticle containing a polylactic acid-glycolic acid copolymer, wherein the statin-included nanoparticle is used to enhance the function of a stem cell. A statin-included nanoparticle preparation containing the statin-included nanoparticle according to the present invention may contain an additive, such as a stabilizing agent, a preservative, a buffer agent, a pH adjustor, and a vehicle generally used for preparation in addition to the statin-included nanoparticle.

In the present invention, statin includes all compounds which are 3-hydroxy-3-methylglutaryl-coenzyme A (HMG-CoA) reductase inhibitors. Examples of statin include simvastatin, rosuvastatin, pitavastatin, atorvastatin, cerivastatin, fluvastatin, pravastatin, lovastatin, and mevastatin. As described above, it is known that statin has hypocholesterolemic activity, and besides this, a large-scale clinical test has revealed that the statin reduces the occurrence and/or the risk of progression of cardiovascular events. Moreover, there have been a large number of reports about neovascularization promoting activity via vascular endothelial cells and/or bone marrow-derived endothelial progenitor cells. It is also known that statin exhibits anti-inflammatory activity.

In the present embodiment, the material of the nanoparticle is not limited as long as statin can be included in the nanoparticle, but nanoparticle containing poly lactic acid (PLA) or poly(lactic co-glycolic acid) (PLGA) is preferably used. The PLA is hydrolyzed in vivo and is decomposed into lactic acid, the PLGA is hydrolyzed in vivo and is decomposed into lactic acid and glycol, which eventually become water and carbon dioxide gas, respectively. The PLA and the PLGA are thus harmless in vivo and are preferable.

In the present invention, statin-included nanoparticles are processed (fabricated) to achieve the following upper and lower limits of a number average particle size when measured by a light scattering method from the point of view of uptake efficiency into stem cells. The upper limit of the number average particle size is smaller than 1000 nm, preferably about 600 nm or smaller (more preferably 600 nm or smaller), more preferably about 400 nm or smaller (much more preferably 400 nm or smaller). The lower limit of the number average particle size is about 100 nm or larger (more preferably 100 nm or larger), preferably about 200 nm or larger (more preferably 200 nm or larger). For example, when measured by the light scattering method, the number average particle size of the statin-included nanoparticles is smaller than 1000 nm, preferably about 100 nm to about 600 nm (more preferably 100 nm to 600 nm), more preferably about 200 nm to about 400 nm (much more preferably 200 nm to 400 nm). In the present invention, the statin-included nanoparticles may be produced by any method as long as the method can process the statin-included nanoparticles so as to satisfy the above-mentioned number average particle size. The statin-included nanoparticles are preferably fabricated by using a spherical crystallization technique. The spherical crystallization technique is known as a method designing a spherical crystal grain by controlling a crystal formation and/or growth process in the final process of a compound synthesis to enable processing of the spherical crystal grain by directly controlling its physical property. One of the spherical crystallization techniques is an emulsion solvent diffusion method (ESD method).

The emulsion solvent diffusion method is performed by using two types of organic solvents, namely, a good solvent and a poor solvent. In the good solvent, a bioabsorbable polymer such as the PLA or the PLGA for inclusion of statin is soluble. In the poor solvent, the polymer is insoluble. First, a polymer such as the PLA or the PLGA is dissolved in the good solvent, and a statin solution is added and mixed with the good solvent without causing precipitation of the polymer, thereby obtaining a mixture. When the mixture is dropped in the poor solvent which is agitated, a rapid mutual diffusion of the good solvent into the poor solvent and the poor solvent into the good solvent occurs, which disturbs the interface between an organic solvent phase and an aqueous phase. Thus, self-emulsification of the good solvent occurs to form emulsion drops each having a submicron size. Then, the mutual distribution of the good solvent and the poor solvent further advances, and solubilities of the polymer such as the PLA or the PLGA and the statin in each of the emulsion drops decreases. As a result, polymer nanoparticles as spherical crystal grains containing statin are produced.

In the present invention, the stem cells are a cell having totipotency, multipotency, or pluripotency. Examples of the stem cells include somatic stem cells such as embryonic stem cells (ES cells), induced pluripotent stem cells (iPS cells), and mesenchymal stem cells. In the present invention, in order to obtain a large number of stem cells more easily and in larger quantity, mesenchymal stem cells obtained from bone marrow tissues, fat tissues, or the like are preferably used. Among them, adipose derived stem cells are particularly preferably used. Administration of the adipose derived stem cells alone has already been clinically performed, and it is known that the adipose derived stem cells differentiate into fat, bones, a liver, a heart, and the like. The adipose derived stem cells can be obtained from fat tissues, and the fat tissues can be easily obtained from, for example, subcutaneous fat by a minimally invasive technique such as liposuction. The adipose derived stem cells can be abundantly collected by being extracted and separated from the thus obtained fat tissues by using Celution system (manufactured by Cytori Therapeutics Inc.) or the like. Thus, the adipose derived stem cells are particularly advantageously used as the stem cells according to the present invention.

Treatment of stem cells with the statin-included nanoparticles according to the present invention is performed by adding the statin-included nanoparticles to, for example, an incubation medium in which the stem cells are incubated. In this way, the statin-included nanoparticles are taken up into the stem cells through phagocytosis, and therefore, the stem cells can easily contain the statin-included nanoparticles without using a particular reagent, and the like.

In stem cells treated with the statin-included nanoparticles according to the present invention, in particular, migratory capacity, proliferative capacity, and immunosuppression capacity are enhanced, and in particular, the therapeutic effect on inflammatory diseases is enhanced. Such functionally enhanced stem cells according to the present invention exhibit an excellent effect with a small administration amount even in a case of the intravenous administration or in a case of the intra-arterial administration. Specifically, when the adipose derived stem cells treated with the statin-included nanoparticles according to the present invention are intra-arterially administered, the adipose derived stem cells are delivered by a blood stream to an organ, for example, intestine, exhibiting inflammation, accumulate and proliferate in inflammation division, produce anti-inflammatory cytokine, and downregulate the activity of inflammatory cells. As a result, excellent therapeutic effect on inflammatory diseases is exhibited.

In the present invention, the term "inflammatory diseases" refers to diseases one of causes of which is inflammation and the term "inflammatory diseases" refers to not only diseases such as enteritis, pneumonia, and the like whose characteristic symptom is inflammation but also diseases such as pulmonary hypertension and dementia whose episode process involves inflammation. Specific examples of the inflammatory diseases in the present invention include inflammatory bowel disease (IBD) such as systemic lupus erythematosus, scleroderma, lichenoid eczema, chronic rheumatoid arthritis, interstitial pneumonia, asthma bronchial, pulmonary hypertension, ulcerative colitis, and Crohn's disease, nerve injury, spinal cord injury, cerebrovascular accident (cerebral infarction and aftereffects of intracerebral breeding), amyotrophic lateral sclerosis, chronic inflammatory demyelinating polyradiculoneuropathy, schizophrenia, dementia, rejection symptom in organ transplantation, and chronic glomerulonephritis (nephrosclerosis).

Moreover, as described above, the adipose derived stem cells hydrolyze the statin-included nanoparticles taken up in the cells to gradually release the included statin. When the adipose derived stem cells are administered to bodies, the adipose derived stem cells perform controlled-release of statin after the administration, and it is possible to obtain a further anti-inflammatory effect due to statin which is released.

EXAMPLES

Examples are shown in detail below to describe statin-included nanoparticles for enhancing a stem cell function, functionally enhanced stem cells containing the statin-included nanoparticles, and the like according to the present invention.

First, a method for producing statin-included nanoparticles will be described. Here, in particular, simvastatin was used as the statin, and nanoparticles containing polylactic acid (PLA) polymers or polylactic acid-glycolic acid (PLGA) copolymers were used as the nanoparticles.

In a mixed solution of 2 mL acetone and 0.5 mL ethanol, 50 mg PLA (weight average molecular weight 20000) and 2.5 mg simvastatin were dissolved to obtain a polymer solution. The polymer solution was dropped in 10 mL 2-wt %-PVA solution agitated at 500 rpm at a room temperature to obtain a simvastatin-included PLA nanoparticle suspension. Subsequently, while the agitation at 500 rpm was continued at the room temperature, organic solvents (acetone and ethanol) were removed by evaporation. After the removal of the solvents by the evaporation for about 5 hours, the suspension was subjected to centrifugal separation performed at 4° C. and at 60000 g for 30 minutes to collect sediments, and resuspension of the sediments in distilled water was performed. The centrifugal separation and the resuspension in the distilled water were performed three times in total. Then, the suspension was freeze-dried for one night to obtain simvastatin-included PLA nanoparticles. In 1 mg nanoparticles, 24.94 μg of simvastatin were included. Simvastatin-included PLGA nanoparticles were obtained in a similar method.

These were adopted as statin-included nanoparticles in the following test.

Next, the following test was performed in order to study the optimal treatment concentration for processing stem cells with the thus obtained statin-included nanoparticles.

In order to conduct the test, first, adipose derived stem cells (AdSC) were obtained from human fat tissues by a known method using collagenase treatment and a centrifugal specific gravity method, and adipose derived cells were obtained from mouse adipose tissues. The details of the method will be described below.

First, a method for obtaining adipose derived stem cells from human fat tissues will be described. A Liberase™ RG solution (0.5 mg/mL=0.47 WU/mL, Sigma 5401127001 50 mg/vial)/HBSS (ThermoFisher 14175095) and a 10× hemolysis solution (8.3 g NH$_4$Cl, 1.2 g NaHCO$_3$, and 200 μL 0.5 M EDTA/100 mL) were prepared in advance. Fat (150 mL) in three 50 mL-suction syringes was moved in a plastic bottle with a nozzle (AS ONE #1-4640-03 wide-mouth washing bottle 1000 ml), and washing with an equivalent PBS(−) and draining were repeated four or five times. The Liberase™ RG solution (50 mg/vial was dissolved with 20 mL HBSS, a half of which, i.e., 10 mL of which was diluted with HBSS 40 mL (total 50 mL), and was then applied to about 150 mL fat tissues) was put in the bottle of a fat solution, was lightly vortexed, and was subjected to shaking incubation at 37° C. for 20 minutes in a constant-temperature bath provided with a shaker. Then, 50 mL of 20% FBS/DMEM F12 were added into the bottle to stop enzyme reaction. A solution layer (sublayer of fat) was collected through the nozzle of the bottle through a cell strainer (100 μm, BD) into a plurality of new 50-mL tubes. Then, centrifugation at 1200 rpm (300 g)×5 min was performed, and supernatant was abandoned. Cell pellets were suspended in a 1 mM EDTA/PBS 40 mL/tube and were then moved through a cell strainer (40 μm, BD) to the same number of new 50-mL tubes. Then, centrifugation at 1200 rpm (300 g)×5 min was performed, and supernatant was abandoned. Cells were suspended with 2 ml of 1-mM EDTA/PBS and collected in one tube, 8 mL of a hemolysis solution were added to and mixed with the cells, and the cells are then stored for 10 minutes in a cool place (On Ice) (hemolysisoperation). After 1 mM EDTA/PBS was added almost to 45 mL, centrifugation at 1200 rpm (300 g)×5 min was performed, and supernatant was abandoned. The cell pellets were suspended with PBS(−) or 10% DMEM F12 and cultured together with 10% DMEM F12 in a 5% CO$_2$ incubator for three or four days, and adherent cells were used as the adipose derived stem cells (AdSC) in experiments (P0). In the case of performing subcultivation, the subcultivation was further performed for three or four days in a proportion of 1:3 to 4 (density of 3000/cm$^2$ to 4000/cm$^2$).

On the other hand, a method for obtaining adipose derived stem cells from mouse adipose tissues is as follows. A collagenase VIII-type (2 mg/mL, Sigma # C2139)/1% BSA HBSS solution was defrosted in advance in a constant-temperature bath with a shaker at 37° C. Moreover, 1 mM EDTA/PBS is prepared by diluting EDTA (0.5 M EDTA, pH 8.0, LifeTechnologies, AM9260G), 10×DPBS, Ca(−), Mg(−)(GIBCO, 14200-166). Then, two or three mice were killed after anesthesia through hemorrhage from their epigastric regions by a syringe (insulin syringe or the like) with a 26 to 29 G needle. Subcutaneous fat (groin to back) was collected and collectively placed on a 3.5-cm culture plate (a drop of physiological saline was put at the center so that the fat tissues were easily taken out). After cutting (20 to 30 times) by scissors into small pieces with the fat tissues being on a lid, the fat tissues were put in a 15-mL tube together with a collagenase solution having the same volume as fat. A cap was closed, and the tube was overturned for mixing and then incubated in a constant-temperature bath with a shaker at 37° C. for 30 minutes. An equivalent amount of a 10% FBS/DMEM F12 medium was added to stop enzyme reaction. A fat layer of the uppermost part was removed by sucking, and then, supernatant was collected through a cell strainer (40 μm, BD, 352340) into a new 50-mL tube. Then, centrifugation at 1200 rpm (250 g)×5 min was performed, and supernatant was abandoned. One mM EDTA/PBS(−) was added into the tube to 10 ml, and the cell pellets were suspended. Then, centrifugation at 1200 rpm (250 g)×5 min was performed, and supernatant was abandoned. The cell pellets were suspended with a 10% FBS/DMEM F12 medium and were then inoculated in a culture plate (P0). Culture was performed in a 5% CO2 incubator for three or four days, and adherent cells were subcultured as AdSC at 1:1 (P1). Culture was performed in a 5% CO$_2$ incubator for four or five days, and adherent cells were subcultured as AdSC at 1:3 (P2). When the cell density was increased to about 80% to 90%, the cells were adopted in the experiments.

After the human adipose derived stem cells were obtained by the above-described method, rhodamine red fluorescent stain-included PLA nanoparticles obtained by including a rhodamine red fluorescent stain, instead of statin, in PLA nanoparticles by the emulsion solvent diffusion method were added to the incubation media of the adipose derived stem cells so as to achieve a final concentration of 20 µg/mL, 50 µg/mL, 80 µg/mL, or 100 µg/mL. One hour (1 h) or two hours (2 h) after the addition, uptake of rhodamine red fluorescent stain-included PLA nanoparticles was observed with a confocal laser fluorescence microscope. Note that nuclei were stained with DAPI by a general method. The results are shown in FIG. 1.

Moreover, a method similar to the above-described method also caused mouse adipose derived stem cells to take up rhodamine red fluorescent stain-included nanoparticles, and the uptake was measured by a flow cytometry (FACS) analysis. Note that PLGA nanoparticles were used as the nanoparticles, the final concentrations of the rhodamine red fluorescent stain-included PLGA nanoparticles were 20 µg/mL, 50 µg/mL, 75 µg/mL, and 100 µg/mL, and 30 minutes after addition of the rhodamine red fluorescent stain-included PLGA nanoparticle, measurement and analysis were performed with a FACS device (BD FACSAria, BD Biosceinces) and analysis software attached to the device. The results are shown in FIG. 2.

As shown in FIG. 1, it can be seen that the rhodamine red fluorescent stain-included PLA nanoparticles were taken up into the human adipose derived stem cells at all the concentrations. Note that the amount of the rhodamine red fluorescent stain-included PLA nanoparticles taken up into the human adipose derived stem cells increases in a treatment-concentration-dependent manner. Moreover, it can also be seen that the amount of the simvastatin-included PLA nanoparticles taken up into the human adipose derived stem cells is larger in the case where the treatment period is one hour than in the case where the treatment period is two hours. In particular, it was confirmed that when the human adipose derived stem cells were treated with the rhodamine red fluorescent stain-included PLA nanoparticles at a concentration of 100 µg/mL, many rhodamine red fluorescent stain-included PLA nanoparticles were taken up into the stem cells.

On the other hand, also in mouse adipose-derived cells, as illustrated in FIG. 2, the rhodamine red fluorescent stain-included PLGA nanoparticles were taken up into the mouse adipose derived stem cells at all the concentrations, and in particular, the amount of the rhodamine red fluorescent stain-included PLGA nanoparticles taken up into the mouse adipose derived stem cells increased in a treatment-concentration-dependent manner.

Then, the following test was performed in order to study whether or not a difference in the uptake of the nanoparticles into the adipose derived stem cells occurred depending on the grain size of the nanoparticles.

First, PLGA nanoparticles having a grain size of 200 nm to 400 nm and PLGA nanoparticles having a grain size of 400 nm to 600 nm were prepared, and in a manner similar to the above-described test, rhodamine red fluorescent stain instead of statin was included in the PLGA nanoparticles by the emulsion solvent diffusion method. Thus, rhodamine red fluorescent stain-included PLGA nanoparticles in each grain size range were prepared. Next, the PLGA nanoparticles thus prepared were added to an incubation medium (10% FBS/DMEM F12) of human adipose derived stem cells to achieve a final concentration of 100 µg/mL. One hour after the addition, uptake of the rhodamine red fluorescent stain-included PLGA nanoparticles was observed with a confocal laser fluorescence microscope. Note that nuclei were stained with DAPI by a general method. The results are shown in FIG. 3.

As shown in FIG. 3, it can be seen that the rhodamine red fluorescent stain-included PLGA nanoparticles were taken up into the human adipose derived stem cells at all the particle sizes. This result suggests that the grain size of the nanoparticles being within a range of 200 nm to 600 nm enables successful uptake into the adipose derived stem cells. Note that the following tests adopted nanoparticles having a number average particle size of about 300 nm.

Next, in order to study how long the adipose derived stem cells having taken up the simvastatin-included nanoparticles take to release statin from the cells, the amount of the statin released into the medium was measured. Here, similarly to the above test, after the human adipose derived stem cells were treated with simvastatin-included PLA nanoparticles at a concentration of 100 µg/mL for one hour, the medium was replaced, and the amount of simvastatin released in the medium was measured 6 hours, 18 hours, 24 hours, 48 hours, 72 hours, 120 hours, 168 hours, and 336 hours after the replacement of the medium. Specifically, the measurement was performed by using a High-pressure Liquid Chromatography (HPLC) method. The measurement results are shown in FIG. 4.

Moreover, by a method similar to the above-described method, a time taken to release statin from the mouse adipose derived stem cells was also measured. Note that in this example, simvastatin-included PLGA nanoparticles at a concentration of 50 µg/mL were processed for 30 minutes. The results are shown in FIG. 5.

As shown in FIG. 4, about 60% of statin were released from the human adipose derived stem cells after 24 hours from the start of the measurement, and it took about 336 hours to release all the statin. From this result, it can be seen that the statin taken up into the human adipose derived stem cells is not rapidly released but is gradually released from the human adipose derived stem cells. Thus, statin can be released over a long time, so that a good therapeutic effect can be expected.

On the other hand, also in mouse adipose-derived cells, as shown in FIG. 5, in a similar manner as in the case of the human adipose derived stem cells, about 60% of statin were released from the mouse adipose derived stem cells after 24 hours from the start of the measurement, and it took about 336 hours to release all the statin. From this result, statin taken up into the mouse adipose derived stem cells is also released over a long time, so that a good therapeutic effect can be expected.

Next, the following test was performed in order to study enhancement of functions such as the migratory capacity and the proliferative capacity of the adipose derived stem cells due to the simvastatin-included nanoparticles.

First, the migratory capacity of the human adipose derived stem cells was studied by using a migratory property test kit (Transwell (registered trademark)). Specifically, the human adipose derived stem cells were inoculated on a porous membrane of each of wells of the Transwell plate at a dose of $5\times10^4$ cells/well, and in a medium, statin-non-included PLA nanoparticles were added to achieve a concentration of 20 µg/mL, or simvastatin-included PLA nanoparticles were added to achieve concentrations of 20 µg/mL, 50 µg/mL, and 100 µg/mL, and the number of cells passed through the membrane of the Transwell after 16 to 18 hours was measured. The results are shown in FIG. 6(a).

As shown in FIG. 6(a), in the case of treatment with 20-µg/mL statin-non-included PLA nanoparticles (PLA20), and in the case of treatment with 20-µg/mL simvastatin-included PLA nanoparticles (PLA-ST20), the migratory property of the human adipose derived stem cells did not change as compared to the case of a control group (Control) without the treatment, whereas in the case of treatment with 50-μg/mL simvastatin-included PLA nanoparticles (Statin50), the migratory property of the human adipose derived stem cells increased. Moreover, treatment with 100-μg/mL simvastatin-included PLA nanoparticles (Statin100) resulted in a reduction in the migratory property of the human adipose derived stem cells. These results show that the simvastatin-included PLA nanoparticles can promote the migratory capacity of the human adipose derived stem cells although there is an optimal treatment concentration.

Next, results of study of an improvement in the proliferation characteristic of the adipose derived stem cells due to the simvastatin-included nanoparticles by an MTT assay will be described.

First, human adipose derived stem cells were inoculated on a 96-well microplate at 5000 cells/well, simvastatin-included PLA nanoparticles were added to achieve a concentration of 20 μg/mL, 50 μg/mL, or 100 μg/mL, the medium was replaced after 48 hours, an MTT solution was added to each well, and after two hours, the absorbance at 450 nm was measured with a spectral photometer. The results are shown in FIG. 6(*b*).

As shown in FIG. 6(*b*), in all the cases of treatment with the simvastatin-included nanoparticles at concentrations of 20 μg/mL (Statin20), 50 μg/mL (Statin50), and 100 μg/mL (Statin100), the proliferation of the human adipose derived stem cells was observed as compared to the case of a control group (Control) without the treatment, but in particular, in the case of the treatment at a concentration of 50 μg/mL, a significant increase in the proliferation characteristic was observed as compared to the control group. These results show that the simvastatin-included PLA nanoparticles can promote the proliferative capacity of the human adipose derived stem cells.

As described above, the enhancement of functions such as the migratory capacity and the proliferative capacity of the adipose derived stem cells due to the statin-included nanoparticles was studied. As a conclusion, the statin-included nanoparticles can enhance the functions of the adipose derived stem cells. When these functions are enhanced, the adipose derived stem cells are advantageous for treating inflammatory diseases.

Next, with a mouse IBD model, the therapeutic effect of stem cells containing the statin-included nanoparticles according to the present invention on inflammatory diseases was studied.

First, an enteritis mouse model using dextran sulfuric acid sodium (DSS) was adopted to study a preferable number of cells administered and administration path of the stem cells according to the present invention. The method and the result will be described below.

First, water containing 2.5% DSS instead of water was continuously administered to C57BJ/6J mice at the age of 6 to 8 weeks for 5 days to cause enteritis, and mouse adipose derived stem cells were intravenously, intraperitoneally, or intra-arterially administered on day 5. Note that as the mouse adipose derived stem cells, cells in which rhodamine red fluorescent stain-included PLGA nanoparticles were taken up in advance in a method similar to the above-described method were used. Specifically, the intra-arterial administration was performed in such a manner that the left common carotid artery distal site of each mouse was ligated with a 6 to 0 silk thread, a site immediately thereunder was sectioned by 2 mm by scissors, and then, a 30 G catheter was inserted. The numbers of cells administered were $2 \times 10^4$ cells, $1 \times 10^5$ cells, and $3 \times 10^5$ cells. Then, the mice were allowed to drink normal water freely from day 5 to day 8. On day 8, the mice were killed painlessly and were subjected to autopsy to take out their large intestines, which were subjected to a histological analysis. Specifically, uptake of the rhodamine red fluorescent stain-included PLGA nanoparticles was observed with a confocal laser fluorescence microscope. Note that nuclei were stained with DAPI by a general method. The results are shown in FIGS. 7 and 8.

As illustrated in FIG. 7, when the mouse adipose derived stem cells were administered intravenously or intraperitoneally, no stem cell stained with rhodamine was observed. In contrast, as illustrated in FIG. 8, when the mouse adipose derived stem cells were intra-arterially administered, the presence of the stem cells (arrowed parts in FIG. 8) was observed when the number of cells administered was larger than $1 \times 10^5$ cells, i.e., it was suggested that the stem cells can accumulate at inflamed intestines.

Next, based on the result, the enteritis depression effect of adipose derived stem cells containing statin-included nanoparticles was studied. The method and the result will be described below.

First, in a similar manner as in the above test, water containing 2.5% DSS instead of water was continuously administered to C57BJ/6J mice at the age of 6 to 8 weeks for 5 days to cause enteritis. On day 5, PBS, mouse adipose derived stem cells containing statin-non-included nanoparticles, or mouse adipose derived stem cells containing statin-included nanoparticles were intra-arterially administered (each group n=6). The dose of the mouse adipose derived stem cells was $2 \times 10^5$ cells/mouse. As the statin-non-included nanoparticles, PLGA was adopted, as the statin-included nanoparticles, the simvastatin-included PLGA nanoparticles were adopted, and 50 μg/mL of these nanoparticles and mouse adipose derived stem cells were co-cultured for 30 minutes to 1 hour to obtain mouse adipose derived stem cells containing statin-non-included nanoparticles or statin-included nanoparticles.

Then, the mice were allowed to drink normal water freely from day 5 to day 8. From day 0 to day 8 after the start of the test, the body weight was measured daily. Moreover, on day 8, the mice were killed painlessly and were subjected to autopsy to take out their large intestines, which were subjected to a histological analysis and the like. Specifically, the length of the large intestines, Disease Activity Index (DAI) score, and the gene expression related to immunoregulation such as inflammatory cytokine were measured.

First, FIG. 9 shows results of body weight measurement of each group are shown. The graph in FIG. 9 shows an increase and a decrease in percentage of the body weight, where the body weight on day 0 is 100%. As illustrated in FIG. 9, the body weights decreased in the same way in the groups from day 5 as a border after DSS caused inflammation in the intestine. However, on and after day 6, as compared to a Control group administered with PBS, the decrement percentage of the body weight was small in a group administered with mouse adipose derived stem cells containing statin-non-included nanoparticles (AdSC group) and a group administered with mouse adipose derived stem cells containing statin-included nanoparticles (Sim-AdSC group), and in particular, in the Sim-AdSC group, a decrease in the body weight was hardly observed.

Next, FIG. 10(*a*) shows a result of measurement of the length of the large intestine. FIG. 10(*b*) shows a result of measurement of the DAI score.

As illustrated in FIG. 10(*a*), the length of the large intestine is long in the order of the Sim-AdSC group, the AdSC group, and the Control group. It is known that when inflammation occurs in the large intestine, the length of the large intestine in general increases. Therefore, it can be seen that the inflammation is suppressed in the order of the Sim-AdSC group, the AdSC group, and the Control group.

Moreover, as illustrated in FIG. 10(b), the DAI score is small in the order of the Sim-AdSC group, the AdSC group, and the control group. The DAI score is a severity of each mouse expressed in a score according to the criteria shown in FIG. 11, and the larger score means the higher severity. Therefore, it can be seen that the inflammation is suppressed in the order of the Sim-AdSC group, the AdSC group, and the Control group.

Next, FIG. 12 shows a result of measurement of gene expression of TNFα, IL-17, IL-6, and IL-1β as cytokines related to immunoregulation such as inflammation in each group. Specifically, in this example, intestine tissues in each group were collected, and the gene expression of TNFα, IL-17, IL-6, and IL-1β of these tissues was analyzed by a quantitative RT-PCR method using a primer specific to each gene of the mouse.

As illustrated in FIG. 12, the gene expression amount of TNFα, IL-17, and IL-1β in the Sim-AdSC group and in the AdSC group significantly decreased as compared to the control group. Moreover, in the gene expression amount of IL-6 in the Sim-AdSC group significantly decreased as compared to the control group and the AdSC group. These results suggest that the adipose derived stem cells containing statin-included nanoparticles cause immunosuppression activity and can suppress inflammation.

FIG. 13 shows results of the histologic analysis in each group. Specifically, in this example, intestine tissues in each group were collected and fixed with a 4% paraformaldehyde solution to create section specimens, and stained with HE. Based on the degree of infiltration of the inflammation cell, the degree of tissue injury was scored (Matts biopsy tissue classification), and the scores were considered by comparison. Note that in the Matts biopsytissue classification, scoring was performed based on the following criteria.
1 Normal Tissue
2 Infiltration of small amount of inflammatory cells in mucous membrane and/or mucous membrane sublayer
3 Infiltration of large amount of inflammatory cells in mucous membrane and/or mucous membrane sublayer
4 Presence of crypto abscess and infiltration of large number of inflammatory cells in all layers of mucous membrane
5 Erosion and/or ulcer and/or necrosis of mucous membrane tissues along with inflammatory cell infiltration FIG. 13(a) shows photographs of stained large intestine pieces of the groups, and FIG. 13(b) is a view illustrating the scores of the stained large intestine pieces of FIG. 13(a).

As illustrated in FIGS. 13(a) and 13(b), it can be seen that the inflammation is suppressed in the order of the Sim-AdSC group, the AdSC group, and the Control group.

Next, with an interstitial pneumonia mouse model, the therapeutic effect of stem cells containing the statin-included nanoparticles according to the present invention on inflammatory diseases was studied. The method and the result will be described below.

As the interstitial pneumonia mouse model, a known model was adopted in which bleomycin was administered to C57B6/J mice with an osmotic pump implanted subcutaneously for continuous infusion, thereby causing interstitial pneumonia. Specifically, first, C57B6/J mice at the age of 6 to 8 weeks were subjected to daily subcutaneous administration of bleomycin at an amount of 100 µg/day for two weeks to cause interstitial pneumonia. Moreover, a week after the start of administration of bleomycin, PBS, mouse adipose derived stem cells containing statin-non-included nanoparticles, or mouse adipose derived stem cells containing statin-included nanoparticles were intravenously administered. The dose of the mouse adipose derived stem cells was $2.5 \times 10^4$ cells/mouse. As the statin-non-included nanoparticles, PLGA was adopted, as the statin-included nanoparticles, the simvastatin-included PLGA nanoparticles were adopted, and 100 µg/mL of these nanoparticles and mouse adipose derived stem cells were co-cultured for 30 minutes to 1 hour to obtain mouse adipose derived stem cells containing statin-non-included nanoparticles or statin-included nanoparticles.

Then, three weeks after the start of the administration of bleomycin, the mice were killed painlessly and were subjected to autopsy to take out their lungs, which were subjected to a histological analysis. Specifically, in this example, lung tissues in each group were collected, fixed with a 4% paraformaldehyde solution to create section specimens, and stained with HE. FIG. 14 shows photographs of stained lung slices of the groups. Note that FIG. 14 also shows a photograph of a lung slice of normal mice to which bleomycin was not been administered.

As illustrated in FIG. 14, in the pulmonary tissues of the normal mice, a large number of unstained cavities were observed in alveolar. However, in lung tissues of mice in which interstitial pneumonia was caused by bleomycin and which was administered with only PBS, regions considered to be inflammatory sites were stained as compared to the normal mice, and a decrease of the cavities was observed. Moreover, in the mice administered with mouse adipose derived stem cells containing statin-non-included nanoparticles (AdSC), stained regions were reduced and the cavities were increased as compared to those in the PBS group. Moreover, in the mice administered with mouse adipose derived stem cells containing statin-included nanoparticles (Sim-AdSC), recovery to a similar extent to the normal mice was observed. These results suggest that the adipose derived stem cells containing statin-included nanoparticles can suppress inflammation also in interstitial pneumonia.

Next, with a scleroderma mouse model, the therapeutic effect of stem cells containing the statin-included nanoparticles according to the present invention on inflammatory diseases was studied. The method and the result will be described below.

As the scleroderma mouse model, a known model was adopted in which BALB/c mice was administered with bleomycin, thereby causing scleroderma. Specifically, first, BALB/c mice at the age of 6 to 8 weeks were subjected to daily subcutaneous administration of bleomycin at an amount of 100 µg/day for three weeks to cause scleroderma. Moreover, a week after the start of administration of bleomycin, PBS, mouse adipose derived stem cells containing statin-non-included nanoparticles ($1.0 \times 10^4$ cells/mouse or $2.5 \times 10^5$ cells/mouse), or mouse adipose derived stem cells containing statin-included nanoparticles ($1.0 \times 10^4$ cells/mouse) were intravenously administered. As the statin-non-included nanoparticles, PLGA was adopted, as the statin-included nanoparticles, the simvastatin-included PLGA nanoparticles were adopted, and 100 µg/mL or 200 µg/mL of these nanoparticles and mouse adipose derived stem cells were co-cultured for 30 minutes to 1 hour to obtain mouse adipose derived stem cells containing statin-non-included nanoparticles or statin-included nanoparticles.

Then, three weeks after the start of the administration of bleomycin, the mice were killed painlessly and were subjected to autopsy to take out their skin tissues, which were subjected to a histological analysis. Specifically, in this example, skin tissues in each group were collected, fixed with a 4% paraformaldehyde solution to create section specimens, and stained with HE. FIG. 15 shows photographs of stained skin slices of the groups. Note that FIG. 15 also shows a photograph of a skin slice of normal mice to which bleomycin was not been administered.

As illustrated in FIG. 15, the presence of epidermis (indicated by the white arrow) was observed in skin tissues of the normal mice. However, in the skin tissues of the mice in which scleroderma was caused by bleomycin and which were administered with only PBS, the epidermis was very thin and dermis part (indicated by the black arrow) was thick as compared to the normal mice. Moreover, in the mice administered with mouse adipose derived stem cells containing statin-non-included nanoparticles (AdSC $1\times10^4$, AdSC $2.5\times10^5$), it can be seen that the thickness of dermis is small as compared to that in the PBS group, and in particular, in the AdSC $2.5\times10^5$ administered with a more amount of stem cells, the thickness of the dermis is smaller. Moreover, in the mice administered with mouse adipose derived stem cells containing statin-included nanoparticles (Sim100-AdSC $1.0\times10^4$, Sim200-AdSC $1.0\times10^4$), it can be seen that the thickness of dermis is small as compared to that in the PBS group, and in particular, in the Sim200-AdSC $1.0\times10^4$ using nanoparticles in which 200 μg/mL statin were included, recovery to an extent close to the thickness of the dermis in the skin tissues of the normal mice was achieved. These results suggest that the adipose derived stem cells containing statin-included nanoparticles can reduce symptoms also in scleroderma.

Next, with a nerve injury mouse model, the therapeutic effect of stem cells containing the statin-included nanoparticles according to the present invention on inflammatory diseases was studied. The method and the result will be described below.

As the nerve injury mouse model, a known model was adopted in which left sciatic nerve of C57B6/J mice was clamped by a forceps for 20 seconds, thereby causing a nerve injury. Specifically, first, skin incision of left buttock of C57B6/J mice at the age of 10 to 12 weeks was performed under anesthesia, intramuscular sarcolemma in the femoral area was peeled to expose left sciatic nerve, and the left sciatic nerve was pressed by a forceps for 20 seconds to cause a nerve injury. Three days after the nerve injury, PBS, mouse adipose derived stem cells containing statin-non-included nanoparticles, or mouse adipose derived stem cells containing statin-included nanoparticles were intravenously administered. The dose of the mouse adipose derived stem cells was $5\times10^4$ cells/mouse. As the statin-non-included nanoparticles, PLGA was adopted, as the statin-included nanoparticles, the simvastatin-included PLGA nanoparticles were adopted, and 100 μg/mL of these nanoparticles and mouse adipose derived stem cells were co-cultured for 30 minutes to 1 hour to obtain mouse adipose derived stem cells containing statin-non-included nanoparticles or statin-included nanoparticles.

Then, a motor function evaluation was performed immediately before the nerve injury, immediately before the administration, one week, two weeks, three weeks, four weeks, and five weeks after the nerve injury. The motor function was evaluated based on a sciatic functional index (SFI). For the SFI, the length (PL) of foot mark of a hind-leg, the distance (TS) from the center of the first toe to the center of the fifth toe, and the distance (IT) from the center of the second toe to the center of the fourth toe of each mouse were measured at both a normal leg (N) on the right and a nerve injured leg (E) on the left and calculated based on the following formula.

$$SFI=38.3\times(EPL-NPL)/NPL+109.5\times(ETS-NTS)/NTS+13.3\times(EIT-NIT)/NIT-8.8$$

A result of measurement of the SFI in each group is shown in the graph in FIG. 16. As illustrated in FIG. 16, it is observed, as compared to mice administered with only PBS, that the SFI was increased and the motion function was recovered in the mice administered with mouse adipose derived stem cells containing statin-non-included nanoparticles (AdSC). Moreover, in the mice administered with mouse adipose derived stem cells containing statin-included nanoparticles (Sim-AdSC), the SFI was further increased, and it was observed that the motion function was further recovered. These results suggest that the adipose derived stem cells containing statin-included nanoparticles can reduce symptoms also in the nerve injury.

Next, with a schizophrenia mouse model, the therapeutic effect of stem cells containing the statin-included nanoparticles according to the present invention on inflammatory diseases was studied. The method and the result will be described below.

As the schizophrenia mouse model, C57B6/J mice with knocked-out schnurri-2 (Shn-2) gene were adopted (RIKEN BRC). It is known that the brain of a Shn-2 knock-out (KO) mouse has characteristics reported in the brain of a schizophrenia patient at a very high similarity ratio (K Takao et al., Neuropsychophamacology (2013), 38, p 1409-1425). In practice, whether or not the action abnormality was shown in nesting action of Shn-2KO mice was studied as compared to normal mice. Here, felt was given to the normal mice (WT) and the Shn-2KO mice, and whether or not they bit the felt and put it as a nest was observed. The results are shown in FIG. 17.

As illustrated in FIG. 17, the normal mice bit all felt and put it in the nest, but the Shn-2KO mice hardly bit felt. Also from this result, the mice whose Shn-2 was knocked out can be used as a schizophrenia model.

Then, with the Shn-2KO mouse model, therapeutic effect of stem cells containing the statin-included nanoparticles according to the present invention on the schizophrenia model was studied. First, to the Shn-2KO mice, PBS, mouse adipose derived stem cells containing statin-non-included nanoparticles, or mouse adipose derived stem cells containing statin-included nanoparticles were intravenously administered. The dose of the mouse adipose derived stem cells was $1\times10^4$ cells/mouse. As the statin-non-included nanoparticles, PLGA was adopted (50 μg), as the statin-included nanoparticles, the simvastatin-included PLGA nanoparticles (20 μg or 50 μg) were adopted, and these nanoparticles and mouse adipose derived stem cells were co-cultured for 30 minutes to 1 hours to obtain mouse adipose derived stem cells containing statin-non-included nanoparticles or statin-included nanoparticles. After the administration, felt was put in a cage of each mouse, and the state of the felt was observed after one week. Moreover, as illustrated in Table 1 below, the state of the felt was scored. FIG. 18 shows an observation result and the score.

TABLE 1

| SCORE | STATE OF FELT |
|---|---|
| 5 | bitten almost no part |
| 4 | bitten ¼ |

TABLE 1-continued

| SCORE | STATE OF FELT |
|---|---|
| 3 | bitten ⅓ |
| 2 | bitten ½ |
| 1 | bitten all parts |
| 0 | nest state |

As illustrated in FIG. 18, in the case of the mice administered with only PBS, almost no nesting action was observed, and a strong symptom of schizophrenia was observed. Moreover, also in the mouse adipose derived stem cells containing statin-non-included nanoparticles (PLGA 50 μg—AdSC), the nesting action was only slightly observed. In contrast, when in the mice administered with mouse adipose derived stem cells containing statin-included nanoparticles, 20 μg of simvastatin-included PLGA nanoparticles were used (SimPLGA 20 μg—AdSC), the nesting action was observed in some of the mice, and the recovery of the symptom was observed. When 50 μg of simvastatin-included PLGA nanoparticles were used (SimPLGA 50 μg—AdSC), the nesting action was observed to an extent closer to that of the normal mice, and the significant recovery of the symptom was observed. These results suggest that the adipose derived stem cells containing statin-included nanoparticles can reduce symptoms also in schizophrenia.

Next, with an osteoarthritis (OA) mouse model, the therapeutic effect of stem cells containing the statin-included nanoparticles according to the present invention on inflammatory diseases was studied. The method and the result will be described below.

As the OA mouse model, a known model was adopted in which right knee joint fore-crucial ligament of each of BALB/c mice was disconnected and inner meniscus was excised. Specifically, the fore-crucial ligament in the right knee joint of each BALB/c nude mouse (male, at the age of 10 weeks) was surgically disconnected, the inner meniscus was excised, and for four days from day 4 after the surgery (from day 4 to 7 post surgery), a wheel motion load at a rotation of about 15000 was applied to each mouse by a rotating wheel to induce the OA. On day 7 post surgery, PBS, human adipose derived stem cells, or human adipose derived stem cells containing statin-included nanoparticles were topically administered to the right knee joint of each mouse by a 29 G injection needle. The dose of the PBS was 10 μL. Moreover, the dose of the human adipose derived stem cells was $1 \times 10^4$ cells/mouse, and as a solvent, 10 μL PBL was used. As the statin-included nanoparticles, the simvastatin-included PLGA nanoparticles were adopted, and 20 μg/mL of these nanoparticles and human adipose derived stem cells ($1 \times 10^4$ cells) were co-cultured for 30 minutes to 1 hour to obtain human adipose derived stem cells containing statin-included nanoparticles. Note that each group n=3.

Two weeks after the administration, the mice were killed painlessly and were subjected to autopsy to take out their right knee articular cartilage tissues, which were subjected to a histological analysis. Specifically, in this example, right knee articular cartilage tissues in each group were collected, fixed with a 4% paraformaldehyde solution to create section specimens, and stained with safranine O. The safranine O is a staining reagent which stains the cartilage matrix. FIG. 19 shows photographs of stained joint cartilage tissue slices of the group. Note that FIG. 19 also shows a photograph of a stained right knee joint cartilage tissues slice of normal mice whose right knee joint fore-crucial ligament was not disconnected and inner meniscus was not excised.

As illustrated in FIG. 19, in the joint cartilage tissues of the normal mice, a thick cartilage layer exists in the bone head part of the shinbone, and a stain with the safranine O was observed (dark gray part). In contrast, in the group (PBS group) in which the mice in which OA was induced and which was administered with PBS, the cartilage layer of the bone head part of the shinbone was very thin, and no stain with the safranine O was observed in the cartilage layer. On the other hand, in a group of mice in which OA was induced and which were administered with human adipose derived stem cells (AdSC group), the cartilage layer of the bone head part of the shinbone was thick and slight stain with the safranine O was observed as compared to the PBS group. Moreover, in a group of mice in which OA was induced and which were administered with human adipose derived stem cells containing statin-included nanoparticles (Statin-AdSC group), the cartilage layer of the bone head part of the shinbone is thicker and more parts stained with the safranine O were observed than in the AdSC group.

Moreover, for the PBS group, the AdSC group, and the Statin-AdSC group, the degree of joint injury was scored in histopathological view. Note that the criteria of the scoring are based on Osteoarthritis and Cartilage 18 (2010) S17-S23, and evaluation was performed as described below.

TABLE 2

| SCORE | PATHOLOGICAL FINDINGS IN CARTILAGE LAYER |
|---|---|
| 0 | normal |
| 0.5 | decrease of regions dyed with safranine O (tissue construction was maintained) |
| 1 | small amount of fibrin deposition (no decrease of cartilage tissues) |
| 2 | crack (limited in cartilage outer layer + a few amount of decrease of the surface thin film) |
| 3 | crack + erosion (reached calcification cartilage layer + equal to or less than 25% of periphery length) |
| 4 | crack + erosion (reached calcification cartilage layer + equal to or less than 25% to 50% of periphery length) |
| 5 | crack + erosion (reached calcification cartilage layer + equal to or less than 50% to 75% of periphery length) |
| 6 | crack + erosion (reached calcification cartilage layer + equal to or more than 75% of periphery length) |

FIG. 20 shows results of scoring of each group based on the criteria of the scoring. As illustrated in FIG. 20, the score is high and the degree of joint injury is high in the PBS group, but the score is lower in the AdSC group than in the PBS group, and moreover, the score is much lower in the Statin-AdSC group. These results suggest that the adipose derived stem cells containing statin-included nanoparticles can reduce symptoms also in osteoarthritis.

Next, with a dementia mouse model, the therapeutic effect of stem cells containing the statin-included nanoparticles according to the present invention on inflammatory diseases was studied. The method and the result will be described below.

As dementia model mice, mice C57BL/6-App<tm3(NL-G-F)Tcs> obtained from Riken BioResource Center were used. The model mice were slowly administered with PBS, adipose derived stem cells, or adipose derived stem cells containing statin-included nanoparticles thorough the caudal vein of the mice. In the test, as the adipose derived stem cells, mouse adipose derived stem cells obtained from subcutaneous fat of the C57BL/6 mice were used. The dose of the adipose derived stem cells was $1 \times 10^4$ cells/mouse, and as a solvent, 200 μL PBL were used. As the statin-included nanoparticles, the simvastatin-included PLGA nanoparticles were adopted, and 20 µg/mL of these nanoparticles and mouse adipose derived stem cells (1×10$^4$ cells) were cultured for 30 minutes at 37° C. to obtain mouse adipose derived stem cells containing statin-included nanoparticles. As the solvent in the administration, 200 µL PBS were used.

The mouse subjected to the administration and a normal wild-type mouse were subjected to the known Barnes maze test for evaluating their memories. Specifically, a time and a migration distance until each mouse finds a target hole provided to only one of 20 circles formed in a peripheral part of a Barnes maze table and reaches an escape cage in communication with the target hole were measured as a memory analysis on day 0, day 7, and day 14, where the date of the administration is day 0. Moreover, memory training was performed once in the morning and once in the afternoon on the day before the measurement (memory analysis) was performed.

Each mouse was bred together with a plurality of mice in one cage, and more than one hour before the memory training and the memory analysis, the mice were separated into individual cages, for adaptation to the environment. In the memory training, each mouse was first left to stand still in a white cylindrical container placed at the center of the maze table for one minutes. Then, the cylindrical container was removed from the maze table, and an ultrasonic warning buzzer which the mouse dislikes was sounded. For three minutes from this, the mouse was let search the target hole, and at a time point when the mouse entered the escape cage, the ultrasonic warning buzzer was stopped. Note that when the mouse did not enter the escape cage after the three minutes has elapsed, the mouse was put in a transparent cylindrical container and was forced to enter the escape cage by taking about 30 seconds to let the mouse watch the surrounding environment to memorize it. For one minutes after the mouse was put in the escape cage, the mouse was adapted to the environment. In the memory training, the above-described process was repeated three times.

In the memory analysis performed on the next day of the memory training, first, in a similar manner to the memory training, a mouse was left to stand still in a white cylindrical container placed at the center of the maze table for one minutes, and then, the cylindrical container was removed from the maze table, and an ultrasonic warning buzzer at a frequency which the mouse dislikes was sounded, and recording of action tracking was started. Then, the mouse searched the target hole, and at a time point when the mouse entered the escape cage, the ultrasonic warning buzzer was stopped, and the recording of the action tracking was stopped. To record the action tracking, LimeLite software (ActiMetrics, Inc. IL, USA) which is an action analysis system was used, and a migration distance (target arrival migration distance) and a time (target arrival time) after the ultrasonic wave warning buzzer was sounded until the mouse entered the escape cage were measured. FIG. 21 shows results of the memory analysis of each mouse.

As illustrated in FIG. 21, on day 0, as compared to the normal mice (WT), the migration distance and the time until the mouse reaches the escape cage were long in each of the dementia model mice administered with PBS (PBS), the dementia model mice administered with adipose derived stem cells (AdSC), and the dementia model mice administered with adipose derived stem cells containing statin-included nanoparticles (SimAdSC). However, as time passes, namely, on day 7 and on day 14, the migration distance and the time until dementia model mice each administered with the adipose derived stem cells or the adipose derived stem cells containing statin-included nanoparticles reached the escape cage became short as compared to the dementia model mice administered with PBS. In particular, in the dementia model mice administered with adipose derived stem cells containing statin-included nanoparticles, a result equivalent to that of normal mice was observed on day 14. These results suggest that the adipose derived stem cells containing statin-included nanoparticles can reduce symptoms also in dementia.

From the above results, the statin-included nanoparticles according to the present invention can enhance the functions of stem cells, and when functionally enhanced stem cells are administered to targets having inflammatory diseases, the stem cells accumulate in inflammatory sites such as intestines, suppress immunity, and exhibit anti-inflammatory activity. Moreover, the stem cells according to the present invention enable controlled release of incorporated statin, thereby obtaining an anti-inflammation effect of the statin itself, and therefore, the stem cells are beneficial for the treatment of inflammatory diseases.

What is claimed is:

1. A method for treating an inflammatory disease in a subject in need thereof, comprising administering a functionally-enhanced adipose-derived stem cell or a cell preparation comprising the functionally enhanced adipose-derived stem cell to the subject,
    wherein the functionally-enhanced adipose-derived stem cell comprises a statin-included nanoparticle comprising:
        a nanoparticle containing a bioabsorbable polymer; and
        a statin included in the nanoparticle, and
    wherein the statin-included nanoparticle is internalized within the adipose-derived stem cell.

2. The method for treating an inflammatory disease of claim 1, wherein the cell preparation comprising the functionally enhanced adipose-derived stem cell according is administered intra-arterially, intravenously, or topically to the subject.

3. The method for treating an inflammatory disease cell of claim 1, wherein the inflammatory disease is inflammatory bowel disease.

4. The method for treating an inflammatory disease cell of claim 1, wherein the inflammatory disease is interstitial pneumonia.

5. The method for treating an inflammatory disease cell of claim 1, wherein the inflammatory disease is scleroderma.

6. The method for treating an inflammatory disease cell of claim 1, wherein the inflammatory disease is nerve injury.

7. The method for treating an inflammatory disease cell of claim 1, wherein the inflammatory disease is schizophrenia.

8. The method for treating an inflammatory disease cell of claim 1, wherein the inflammatory disease is osteoarthritis.

9. The method for treating an inflammatory disease cell of claim 1, wherein the inflammatory disease is dementia.

* * * * *

UNITED STATES PATENT AND TRADEMARK OFFICE
CERTIFICATE OF CORRECTION

PATENT NO. : 10,842,876 B2
APPLICATION NO. : 16/098838
DATED : November 24, 2020
INVENTOR(S) : Masaaki Ii et al.

It is certified that error appears in the above-identified patent and that said Letters Patent is hereby corrected as shown below:

On the Title Page

On Page 2, Column 2, Item (56), Line 8, under Other Publications, delete "AdiposeDerived" and insert --Adipose-Derived--.

On Page 2, Column 2, Item (56), Line 24, under Other Publications, delete "Simvastin" and insert --Simvastatin--.

On Page 2, Column 2, Item (56), Line 25, under Other Publications, delete "Biodegradeable" and insert --Biodegradable--.

In the Specification

In Column 2, Line 26, delete "Gonzalez, M A" and insert --Gonzalez, MA--.

In Column 3, Line 36, delete "acid" and insert --acid)--.

In Column 10, Line 15, delete "(hemolysisoperation)." and insert --(hemolysis operation).--.

In Column 10, Line 57, delete "CO2" and insert --$CO_2$--.

In Column 11, Line 2, delete "adipose derived" and insert --adipose-derived--.

In Column 11, Line 4, delete "(1 h)" and insert --(1h)--.

In Column 11, Line 5, delete "(2 h)" and insert --(2h)--.

In Column 11, Line 21, delete "Biosceinces)" and insert --Biosciences)--.

In Column 15, Line 37, delete "biopsytissue" and insert --biopsy tissue--.

Signed and Sealed this
Sixth Day of April, 2021

Drew Hirshfeld
*Performing the Functions and Duties of the
Under Secretary of Commerce for Intellectual Property and
Director of the United States Patent and Trademark Office*

In Column 15, Line 47, delete "infiltration" and insert --infiltration.--.

In Column 18, Line 30, delete "Neuropsychophamacology" and insert --Neuropsychopharmacology--.

In Column 21, Line 50, delete "LimeLite" and insert --LimeLight--.

In Column 22, Line 3, delete "(SimAdSC)." and insert --(Sim-AdSC).--.

In the Claims

In Column 22, Line 42, Claim 2, delete "cell according" and insert --cell--.